US008187835B2

(12) United States Patent
Itaya et al.

(10) Patent No.: US 8,187,835 B2
(45) Date of Patent: May 29, 2012

(54) METHOD FOR PRODUCING PROTEIN

(75) Inventors: Hiroshi Itaya, Kawasaki (JP); Yoshimi Kikuchi, Kawasaki (JP); Masayo Date, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/938,844

(22) Filed: Nov. 13, 2007

(65) Prior Publication Data

US 2008/0160575 A1    Jul. 3, 2008

Related U.S. Application Data

(63) Continuation of application No. PCT/JP2006/309598, filed on May 12, 2006.

(30) Foreign Application Priority Data

May 12, 2005  (JP) ................................. 2005-139798

(51) Int. Cl.
*C12N 15/11* (2006.01)
*C12N 15/20* (2006.01)
*C12N 15/24* (2006.01)
(52) U.S. Cl. ..................... 435/69.1; 435/69.7; 435/69.8; 435/69.51; 435/69.52
(58) Field of Classification Search .................. None
See application file for complete search history.

(56) References Cited

U.S. PATENT DOCUMENTS

| 2004/0214296 A1 | 10/2004 | Asahara et al. |
| 2005/0202544 A1 | 9/2005 | Retallack et al. |

FOREIGN PATENT DOCUMENTS

| CN | 1530438 A | 9/2004 |
| JP | 2000-515725 A | 11/2000 |
| JP | 2001-506973 A | 5/2001 |
| JP | 2003-61687 | 3/2003 |
| JP | 2003-153695 | 5/2003 |
| JP | 2004-208537 | 7/2004 |
| WO | WO 97/41221 A1 | 11/1997 |
| WO | WO 98/13497 A1 | 4/1998 |
| WO | WO 98/18946 | 5/1998 |
| WO | WO 00/64247 A1 | 11/2000 |
| WO | WO 03/046226 A1 | 6/2003 |
| WO | WO 2004/005221 A2 | 1/2004 |
| WO | WO 2004/037998 A2 | 5/2004 |

OTHER PUBLICATIONS

Trotsenko, Metabolic Features of Methane- and Methanol-Utilizing Bacteria, Acta Biotechnology, vol. 3, 1983, pp. 2269-2277.*
Marchenko et al Cloning and expression of mosquitocidal endotoxin gene cryIVB from *Bacillus thuringiensis* var israelensis in the obligate methylotroph *Methylobacillus flagellatum*. Journal of Industrial Microbiology & Biotechnology (2000) 24, 14-18.*
Juerg F. Tschopp, et al., "Expression of the IacZ gene from two methanol-regulated promoters in *Pichia pastoris*", Nucleic Acids Research, vol. 15, No. 9, 1987, pp. 3859-3876.

Thomas Vedvick, et al., "High-level secretion of biologically active aprotinin from the yeast *Pichia pastoris*", Journal of Industrial Microbiology, Society for Industrial Microbiology, Elsevier, vol. 7, No. 3, SIM 00328, Apr. 1991, 6 pages.
Marianne M. Figueira, et al., "Production of green fluorescent protein by the methylotrophic bacterium *Methylobacterium extorquens*", FEMS Microbiology Letters, Elsevier, vol. 193/2, Z53-X109, Dec. 15, 2000, 7 pages.
L. Belanger, et al. "Production of heterologous protein by *Methylobacterium* extorquens in high cell density fermentation." FEMS Microbiology Letters, vol. 231, 2004, pp. 197-204.
G.Galliciotti, et al., "Signal-sequence Trap in Mammalian and Yeast Cells: A Comparison", J. Membrane Biol. vol. 183, 2001, pp. 175-182.
Nguan Soon, et al., "Engineering a novel secretion signal for cross-host recombinant protein expression", Protein Engineering, vol. 15, No. 4, 2002, pp. 337-345.
Savvas C. Makrides, "Strategies for Achieving High-Level Expression of Genes in *Escherichia coli*", Microbiological Reviews, vol. 60, No. 3, Sep. 1996, pp. 512-538.
Edward De Maeyer, et al., Expression of a chemically synthesized human α1 interferon gene, Proc. Natl. Acad. Sci. USA, vol. 79, Jul. 1982, pp. 4256-4259.
Sumio Ohta, et al., "Methanol Dehydrogenase of *Methylomonas* J: Purification, Crystallization, and Some Properties", J. Biochem. 90, 205-213 (1981).
Theresa A. Fassel, et al., "Localization of Methanol Dehydrogenase in Two Strains of Methylotrophic Bacteria Detected by Immunogold Labeling", Applied and Environmental Microbiology, Jul. 1992, p. 2302-2307.
Nobuki Hayase, et al. "Secretion of human Epidermal Growth Factor (EGF) in Autotrophic Culture by a Recombinant Hydrogen-Utilizing Bacterium, *Pseudomonas pseudoflava*, Carrying Broad-Host-Range EGF Secreation Vector pKSEGF2" Applied and Environmental Microbiology, American Society for Microbiology, vol. 60, No. 9, Sep. 1994, pp. 3336-3342. Kelly A. Fitzgerald, et al. "Overexpression of Heterologous Protein, Haloalkane Dehalogenase, in a Poly-β-Hydroxybutyrate-Deficient Strain of the Facultative Methylotroph Methylobacterium extorquens Am1" Biotechnology & Bioengineering, Vo. 81, No. 3, Feb. 5, 2003, pp. 263-268 and a Cover Page.
Julian A. Chesshyre, et al. "Low temperatures stabilize interferon α-2 against proteolysis in *Methylophilus methylotrophus* and *Escherichia coli*" Applied Microbiology and Biotechnology, vol. 31 No. 2, Aug. 1989, pp. 158-162 and Cover Page.
N. D. Marchenko, et al. Cloning and expression of mosquitocidal endotoxin gene cryIVB from *Bacillus thuringiensis* var israelensis in the obligate methylotroph *Methylobacillus flagellatum*, Journal of Industrial Microbiology & Biotechnology, vol. 24, No. 1, Jan. 2000, pp. 14-18 and Cover Page.
Jorge Gutiérrez, et al. "Heterologous extracellular production of enterocin P from *Enterococcus faecium* P13 in the methylotrophic bacterium *Methylobacterium* extorquens" FEMS Microbiology Letters, vol. 248, No. 1, pp. 125-131 and Cover Page, 2005.

(Continued)

*Primary Examiner* — Kagnew H Gebreyesus
(74) *Attorney, Agent, or Firm* — Oblon, Spivak, McClelland, Maier & Neustadt, L.L.P.

(57) ABSTRACT

By culturing a methanol-assimilating bacterium which harbors a DNA construct which contains a promoter sequence that functions in the methanol-assimilating bacterium and a nucleotide sequence that encodes a polypeptide containing a signal sequence and an objective protein which is functionally connected to the promoter sequence, in a liquid medium containing methanol as a major carbon source, the bacterium is allowed to secrete the objective protein, and the secreted objective protein is recovered.

11 Claims, No Drawings

OTHER PUBLICATIONS

G. Miksch, et al., "The *kil* gene of the CoIE1 plasmid of *Escherichia coli* controlled by a growth-phase-dependent promoter mediates the secretion of a heterologous periplasmic protein during the stationary phase", Arch Microbiol (1997) 167:143-150.

G. Miksch, et al., "Overexpression of the phytase from *Escherichia coli* and its extracellular production in bioreactors", Appl Microbiol Biotechnol (2002) 59:685-694.

Notice of Reasons for Rejection issued Nov. 4, 2010 in corresponding Chinese Application No. 200680016316.6 (w/English Translation).

Notice of Reasons for Rejection issued Nov. 8, 2010 in corresponding Russian Application No. 2007146174 (w/English Translation).

Takako Yoshida, et al., "Genes involved in the synthesis of the exopolysaccharide methanolan by the obligate methylotroph *Methylobacillus* sp. strain 12S", Microbiology (2003), 149, 431-444.

Sara M. Machlin, et al., "Nucleotide Sequence and Transcriptional Start Site of the *Methylobacterium organophilum* XX Methanol Dehydrogenase Structural Gene", Journal of Bacteriology, Oct. 1998, vol. 170, No. 10, p. 4739-4747.

L. I. Patrushev, "Artificial genetic systems." Genetic and protein engineering, vol. 1, 2004, pp. 118-119.

Japanese Office Action (with English translation) issued Sep. 6, 2011, in connection with corresponding Japanese Patent Application No. 2007-528343.

\* cited by examiner

SEQUENCE LISTING

```
<160> NUMBER OF SEQ ID NOS: 39

<210> SEQ ID NO 1
<211> LENGTH: 30
<212> TYPE: DNA
<213> ORGANISM: Artificial sequence
<220> FEATURE:
<223> OTHER INFORMATION: PCR primer

<400> SEQUENCE: 1
aacgggtggc tactacagcc agcacaacag                               30

<210> SEQ ID NO 2
<211> LENGTH: 30
<212> TYPE: DNA
<213> ORGANISM: Artificial sequence
<220> FEATURE:
<223> OTHER INFORMATION: PCR primer

<400> SEQUENCE: 2
ttttcagcca cgatcaggtt gccgttttcg                               30

<210> SEQ ID NO 3
<211> LENGTH: 57
<212> TYPE: DNA
<213> ORGANISM: Artificial sequence
<220> FEATURE:
<223> OTHER INFORMATION: Synthetic DNA

<400> SEQUENCE: 3
aattcgagct cggtacccgg ggatcctcta gagtcgacct gcaggcatgc aagctta    57

<210> SEQ ID NO 4
<211> LENGTH: 57
<212> TYPE: DNA
<213> ORGANISM: Artificial sequence
<220> FEATURE:
<223> OTHER INFORMATION: Synthetic DNA

<400> SEQUENCE: 4
gatctaagct tgcatgcctg caggtcgact ctagaggatc cccgggtacc gagctcg    57
```

<210> SEQ ID NO 5
<211> LENGTH: 30
<212> TYPE: DNA
<213> ORGANISM: Artificial sequence
<220> FEATURE:
<223> OTHER INFORMATION: PCR primer

<400> SEQUENCE: 5
ctatgatcat ttgcctggcg gcagtagcgc                              30

<210> SEQ ID NO 6
<211> LENGTH: 31
<212> TYPE: DNA
<213> ORGANISM: Artificial sequence
<220> FEATURE:
<223> OTHER INFORMATION: PCR primer

<400> SEQUENCE: 6
cttagatctc aaaaagagtt tgtagaaacg c                            31

<210> SEQ ID NO 7
<211> LENGTH: 23
<212> TYPE: DNA
<213> ORGANISM: Artificial sequence
<220> FEATURE:
<223> OTHER INFORMATION: PCR primer

<400> SEQUENCE: 7
cagagtgagc cggagctgaa gct                                     23

<210> SEQ ID NO 8
<211> LENGTH: 23
<212> TYPE: DNA
<213> ORGANISM: Artificial sequence
<220> FEATURE:
<223> OTHER INFORMATION: PCR primer

<400> SEQUENCE: 8
acagttcttc gtttgtcatc agc                                     23

<210> SEQ ID NO 9
<211> LENGTH: 26
<212> TYPE: DNA
<213> ORGANISM: Artificial sequence
<220> FEATURE:
<223> OTHER INFORMATION: PCR primer

<400> SEQUENCE: 9
ctgttcctgc acctgcatgg catggc                                  26

<210> SEQ ID NO 10
<211> LENGTH: 46
<212> TYPE: DNA
<213> ORGANISM: Artificial sequence
<220> FEATURE:
<223> OTHER INFORMATION: PCR primer

<400> SEQUENCE: 10
agcttcagct ccggctcact ctgtgccaca gccaggccgg aaatgc            46

<210> SEQ ID NO 11
<211> LENGTH: 1000
<212> TYPE: DNA
<213> ORGANISM: Methylophilus methylotrophus
<220> FEATURE:
<223> OTHER INFORMATION: methanol dehydrogenase promoter

<400> SEQUENCE: 11

```
ctgttcctgc acctgcatgg catggcgcgc caatacccctg tttctttca gtgtacgctc      60
aagatcttgc tctaccaggc attgctcggt catatcgacc agataaccat gaatctgggc     120
agcatcatga atatcttcag ccgggacgta aataaagcgg cgccgacat agcaaggcaa      180
cccatccggc cgacggatct gcagtttatt gaaattgatt tccttgtgat gctgcaactg     240
cagcacaaac tccggccaat gaaaagaaaa cagacggctg gcattgcggt tggtgctgag     300
cgggcggcag atacggtcaa agcacgatt atgcatgcca atattgcctt caacatccag      360
caccacgttg cccgtcaggt cgccatcaaa agcgtgata tagagttgct ggctgttgcg      420
taactgcatt tcagtttgtt tgcggcgctg aatttctgcg tggatctcct gcatgcgtcg     480
ctggctgaac cacacactca gtaacacaaa cacaaacagg gtgagcggga tttcatccag    540
ttgggcatat tcataggtca gcagccaggc ggtgacacgt tcggccaagt caaattgtga     600
cgacaaaaca aaagtcagtg ccacgcctgc gatcacgatg agcgtgtcac gactggagcg     660
gcttaattg cccagctttt gaatgtcagt aatcacaggg atagaccggt tataagaatg     720
catgatgagg tgaccaaata cttccaaatt gcttctgcac gcgaatatga gggtcatgta    780
cagacatgcg cactatagac cacattcatt gccattgccc cgtgaaaaat tccctttatt    840
ggccggtctg taggaatgaa ttcttgaatc catcataggg aatctttcat ctattgcctt    900
tgttagaaat tattaacaat tcggttcgtg aagtgcggca ttcggggggg tgtctgccac    960
aacacttaaa aaacgcattc ttaagagatt gggagaaagt                           1000
```

<210> SEQ ID NO 12
<211> LENGTH: 151
<212> TYPE: DNA
<213> ORGANISM: Escherichia coli
<220> FEATURE:
<223> OTHER INFORMATION: tac promoter

<400> SEQUENCE: 12

```
cccgttctgg ataatgtttt ttgcgccgac atcataacgg ttctggcaaa tattctgaaa      60
tgagctgttg acaattaatc atcggctcgt ataatgtgtg gaattgtgag cggataacaa     120
tttcaccctg caggcaaagg agatgagcgt a                                    151
```

<210> SEQ ID NO 13
<211> LENGTH: 1722
<212> TYPE: DNA
<213> ORGANISM: Methylophilus methylotrophus
<220> FEATURE:
<223> OTHER INFORMATION: methanol dehydrogenase gene
<220> FEATURE:
<221> NAME/KEY: CDS
<222> LOCATION: (1)..(1722)

<400> SEQUENCE: 13

```
atg gca gat gca gac ctg gac aag cag gtg aat aca gcc ggt gct tgg        48
Met Ala Asp Ala Asp Leu Asp Lys Gln Val Asn Thr Ala Gly Ala Trp
1               5                   10                  15 cca att gca acg ggt ggc tac tac agc cag cac aac agt ccg ctg gca        96
Pro Ile Ala Thr Gly Gly Tyr Tyr Ser Gln His Asn Ser Pro Leu Ala
            20                  25                  30 caa att aac aaa tcc aac gtt aaa aac gtc aaa gca gcc tgg tca ttt       144
Gln Ile Asn Lys Ser Asn Val Lys Asn Val Lys Ala Ala Trp Ser Phe
        35                  40                  45 tca acg ggt gtc ttg aat ggt cac gaa ggt gcg cca ttg gtc atc ggt       192
Ser Thr Gly Val Leu Asn Gly His Glu Gly Ala Pro Leu Val Ile Gly
    50                  55                  60
```

```
gac atg atg tat gtg cac tcc gct ttt cca aac aat act tat gcg ctg       240
Asp Met Met Tyr Val His Ser Ala Phe Pro Asn Asn Thr Tyr Ala Leu
65              70                  75                  80 aat ctg aac gat cca ggc aag att gtc tgg caa cac aag cct aag caa       288
Asn Leu Asn Asp Pro Gly Lys Ile Val Trp Gln His Lys Pro Lys Gln
                85                  90                  95 gat gct tcc acc aaa gcc gtg atg tgc tgt gac gtg gtt gac cgt ggt       336
Asp Ala Ser Thr Lys Ala Val Met Cys Cys Asp Val Val Asp Arg Gly
            100                 105                 110 ctg gct tac ggc gcg ggg caa att gtt aaa aaa caa gcc aac ggt cac       384
Leu Ala Tyr Gly Ala Gly Gln Ile Val Lys Lys Gln Ala Asn Gly His
        115                 120                 125 ttg ctg gcg ttg gat gcc aaa act ggc aaa atc aac tgg gaa gta gaa       432
Leu Leu Ala Leu Asp Ala Lys Thr Gly Lys Ile Asn Trp Glu Val Glu
130                 135                 140 gtg tgt gat cca aaa gtg ggt tca aca ctg aca caa gcg cct ttt gtg       480
Val Cys Asp Pro Lys Val Gly Ser Thr Leu Thr Gln Ala Pro Phe Val
145                 150                 155                 160 gct aaa gac acg gta ttg atg ggg tgt tca ggt gct gag ctg ggt gta       528
Ala Lys Asp Thr Val Leu Met Gly Cys Ser Gly Ala Glu Leu Gly Val
                165                 170                 175 cgt ggt gct gtg aac gcc ttt gac ctg aaa aca ggt gaa ttg aaa tgg       576
Arg Gly Ala Val Asn Ala Phe Asp Leu Lys Thr Gly Glu Leu Lys Trp
            180                 185                 190 cgt gca ttt gca acc ggt tct gat gac tct gtt cgc ctg gcc aaa gac       624
Arg Ala Phe Ala Thr Gly Ser Asp Asp Ser Val Arg Leu Ala Lys Asp
        195                 200                 205 ttc aac agt gca aac cca cat tac ggt caa ttc ggc ctg ggg act aaa       672
Phe Asn Ser Ala Asn Pro His Tyr Gly Gln Phe Gly Leu Gly Thr Lys
210                 215                 220 acc tgg gaa ggc gat gcc tgg aaa att ggt ggc ggt acc aac tgg ggt       720
Thr Trp Glu Gly Asp Ala Trp Lys Ile Gly Gly Gly Thr Asn Trp Gly
225                 230                 235                 240 tgg tat gcc tat gac cct aaa ttg aac ctg ttc tac tac ggt tca ggt       768
Trp Tyr Ala Tyr Asp Pro Lys Leu Asn Leu Phe Tyr Tyr Gly Ser Gly
                245                 250                 255 aac ccg gcc cca tgg aac gaa acc atg cgt cct ggc gac aac aag tgg       816
Asn Pro Ala Pro Trp Asn Glu Thr Met Arg Pro Gly Asp Asn Lys Trp
            260                 265                 270 acg atg acc atc tgg ggt cgt gac ctc gac acc ggc atg gcg aaa tgg       864
Thr Met Thr Ile Trp Gly Arg Asp Leu Asp Thr Gly Met Ala Lys Trp
        275                 280                 285 ggc tac caa aaa acg ccg cat gat gag tgg gac ttt gct ggt gtg aat       912
Gly Tyr Gln Lys Thr Pro His Asp Glu Trp Asp Phe Ala Gly Val Asn
290                 295                 300 cag atg gtg ctg act gat caa cca gtc aac ggc aaa atg acg ccg ctg       960
Gln Met Val Leu Thr Asp Gln Pro Val Asn Gly Lys Met Thr Pro Leu
305                 310                 315                 320 ctg agc cac atc gac cgt aac ggt atc ttg tac aca ctg aac cgc gaa      1008
Leu Ser His Ile Asp Arg Asn Gly Ile Leu Tyr Thr Leu Asn Arg Glu
                325                 330                 335 aac ggc aac ctg atc gtg gct gaa aaa gtg gac ccg gct gtc aac gtg      1056
Asn Gly Asn Leu Ile Val Ala Glu Lys Val Asp Pro Ala Val Asn Val
            340                 345                 350 ttc aaa aaa gtg gac ctg aaa act ggg aca cca gtc cgt gac ccg gaa      1104
Phe Lys Lys Val Asp Leu Lys Thr Gly Thr Pro Val Arg Asp Pro Glu
        355                 360                 365 ttc gcg aca cgt atg gac cat aaa ggc acc aac att tgt cca tcc gcg      1152
Phe Ala Thr Arg Met Asp His Lys Gly Thr Asn Ile Cys Pro Ser Ala
370                 375                 380
```

```
atg ggc ttc cac aac cag ggt gtt gac tct tac gat cca gaa agc cgc      1200
Met Gly Phe His Asn Gln Gly Val Asp Ser Tyr Asp Pro Glu Ser Arg
385                 390                 395                 400 acc ttg tac gct ggc ctg aac cac att tgt atg gat tgg gag ccg ttc      1248
Thr Leu Tyr Ala Gly Leu Asn His Ile Cys Met Asp Trp Glu Pro Phe
                405                 410                 415 atg ctg cca tac cgt gcc ggt cag ttc ttc gtt ggt gca acg ctg gcg      1296
Met Leu Pro Tyr Arg Ala Gly Gln Phe Phe Val Gly Ala Thr Leu Ala
            420                 425                 430 atg tac cct ggc ccg aac ggc cca acc aag aaa gaa atg ggt cag att      1344
Met Tyr Pro Gly Pro Asn Gly Pro Thr Lys Lys Glu Met Gly Gln Ile
        435                 440                 445 cgt gca ttt gac ctg acc act ggt aaa gct aaa tgg act aag tgg gag      1392
Arg Ala Phe Asp Leu Thr Thr Gly Lys Ala Lys Trp Thr Lys Trp Glu
    450                 455                 460 aaa ttc gcg gct tgg ggc ggt act ttg tac acc aaa ggt ggc ctg gtt      1440
Lys Phe Ala Ala Trp Gly Gly Thr Leu Tyr Thr Lys Gly Gly Leu Val
465                 470                 475                 480 tgg tat gca acg ctg gat ggt tac ctg aaa gcc ttg gat aac aaa gac      1488
Trp Tyr Ala Thr Leu Asp Gly Tyr Leu Lys Ala Leu Asp Asn Lys Asp
                485                 490                 495 ggt aaa gag ctg tgg aac ttc aag atg cca tct ggt ggt atc gga tcg      1536
Gly Lys Glu Leu Trp Asn Phe Lys Met Pro Ser Gly Gly Ile Gly Ser
            500                 505                 510 cca atg act tac tcc ttt aaa ggc aag caa tac atc ggc agc atg tac      1584
Pro Met Thr Tyr Ser Phe Lys Gly Lys Gln Tyr Ile Gly Ser Met Tyr
        515                 520                 525 ggt gtt ggc ggc tgg cct ggc gtg ggt ctg gtg ttt gac ctg aca gac      1632
Gly Val Gly Gly Trp Pro Gly Val Gly Leu Val Phe Asp Leu Thr Asp
    530                 535                 540 ccg agt gct ggt ttg ggt gcg gtg ggt gcg ttc aga gaa ctg caa aac      1680
Pro Ser Ala Gly Leu Gly Ala Val Gly Ala Phe Arg Glu Leu Gln Asn
545                 550                 555                 560 cac aca caa atg ggc ggt ggc ctg atg gtg ttc agc ctg taa              1722
His Thr Gln Met Gly Gly Gly Leu Met Val Phe Ser Leu
                565                 570

<210> SEQ ID NO 14
<211> LENGTH: 573
<212> TYPE: PRT
<213> ORGANISM: Methylophilus methylotrophus
<220> FEATURE:
<223> OTHER INFORMATION: methanol dehydrogenase protein

<400> SEQUENCE: 14

Met Ala Asp Ala Asp Leu Asp Lys Gln Val Asn Thr Ala Gly Ala Trp
1               5                   10                  15

Pro Ile Ala Thr Gly Gly Tyr Tyr Ser Gln His Asn Ser Pro Leu Ala
            20                  25                  30

Gln Ile Asn Lys Ser Asn Val Lys Asn Val Lys Ala Ala Trp Ser Phe
        35                  40                  45

Ser Thr Gly Val Leu Asn Gly His Glu Gly Ala Pro Leu Val Ile Gly
    50                  55                  60

Asp Met Met Tyr Val His Ser Ala Phe Pro Asn Asn Thr Tyr Ala Leu
65                  70                  75                  80

Asn Leu Asn Asp Pro Gly Lys Ile Val Trp Gln His Lys Pro Lys Gln
                85                  90                  95

Asp Ala Ser Thr Lys Ala Val Met Cys Cys Asp Val Val Asp Arg Gly
            100                 105                 110
```

```
Leu Ala Tyr Gly Ala Gly Gln Ile Val Lys Gln Ala Asn Gly His
            115                 120                 125
Leu Leu Ala Leu Asp Ala Lys Thr Gly Lys Ile Asn Trp Glu Val Glu
130                 135                 140
Val Cys Asp Pro Lys Val Gly Ser Thr Leu Thr Gln Ala Pro Phe Val
145                 150                 155                 160
Ala Lys Asp Thr Val Leu Met Gly Cys Ser Gly Ala Glu Leu Gly Val
                165                 170                 175
Arg Gly Ala Val Asn Ala Phe Asp Leu Lys Thr Gly Glu Leu Lys Trp
                180                 185                 190
Arg Ala Phe Ala Thr Gly Ser Asp Asp Ser Val Arg Leu Ala Lys Asp
            195                 200                 205
Phe Asn Ser Ala Asn Pro His Tyr Gly Gln Phe Gly Leu Gly Thr Lys
210                 215                 220
Thr Trp Glu Gly Asp Ala Trp Lys Ile Gly Gly Thr Asn Trp Gly
225                 230                 235                 240
Trp Tyr Ala Tyr Asp Pro Lys Leu Asn Leu Phe Tyr Tyr Gly Ser Gly
                245                 250                 255
Asn Pro Ala Pro Trp Asn Glu Thr Met Arg Pro Gly Asp Asn Lys Trp
            260                 265                 270
Thr Met Thr Ile Trp Gly Arg Asp Leu Asp Thr Gly Met Ala Lys Trp
            275                 280                 285
Gly Tyr Gln Lys Thr Pro His Asp Glu Trp Asp Phe Ala Gly Val Asn
            290                 295                 300
Gln Met Val Leu Thr Asp Gln Pro Val Asn Gly Lys Met Thr Pro Leu
305                 310                 315                 320
Leu Ser His Ile Asp Arg Asn Gly Ile Leu Tyr Thr Leu Asn Arg Glu
                325                 330                 335
Asn Gly Asn Leu Ile Val Ala Glu Lys Val Asp Pro Ala Val Asn Val
            340                 345                 350
Phe Lys Lys Val Asp Leu Lys Thr Gly Thr Pro Val Arg Asp Pro Glu
            355                 360                 365
Phe Ala Thr Arg Met Asp His Lys Gly Thr Asn Ile Cys Pro Ser Ala
            370                 375                 380
Met Gly Phe His Asn Gln Gly Val Asp Ser Tyr Asp Pro Glu Ser Arg
385                 390                 395                 400
Thr Leu Tyr Ala Gly Leu Asn His Ile Cys Met Asp Trp Glu Pro Phe
                405                 410                 415
Met Leu Pro Tyr Arg Ala Gly Gln Phe Phe Val Gly Ala Thr Leu Ala
            420                 425                 430
Met Tyr Pro Gly Pro Asn Gly Pro Thr Lys Lys Glu Met Gly Gln Ile
            435                 440                 445
Arg Ala Phe Asp Leu Thr Thr Gly Lys Ala Lys Trp Thr Lys Trp Glu
            450                 455                 460
Lys Phe Ala Ala Trp Gly Gly Thr Leu Tyr Thr Lys Gly Gly Leu Val
465                 470                 475                 480
Trp Tyr Ala Thr Leu Asp Gly Tyr Leu Lys Ala Leu Asp Asn Lys Asp
                485                 490                 495
Gly Lys Glu Leu Trp Asn Phe Lys Met Pro Ser Gly Gly Ile Gly Ser
            500                 505                 510
Pro Met Thr Tyr Ser Phe Lys Gly Lys Gln Tyr Ile Gly Ser Met Tyr
            515                 520                 525
Gly Val Gly Gly Trp Pro Gly Val Gly Leu Val Phe Asp Leu Thr Asp
            530                 535                 540
```

-continued

```
Pro Ser Ala Gly Leu Gly Ala Val Gly Ala Phe Arg Glu Leu Gln Asn
545                 550                 555                 560

His Thr Gln Met Gly Gly Gly Leu Met Val Phe Ser Leu
                565                 570

<210> SEQ ID NO 15
<211> LENGTH: 1299
<212> TYPE: DNA
<213> ORGANISM: Escherichia coli
<220> FEATURE:
<223> OTHER INFORMATION: phytase gene
<220> FEATURE:
<221> NAME/KEY: CDS
<222> LOCATION: (1)..(1299)

<400> SEQUENCE: 15 atg aaa gcg atc tta atc cca ttt tta tct ctt ctg att ccg tta acc      48
Met Lys Ala Ile Leu Ile Pro Phe Leu Ser Leu Leu Ile Pro Leu Thr
1               5                   10                  15 ccg caa tct gca ttc gct cag agt gag ccg gag ctg aag ctg gaa agt      96
Pro Gln Ser Ala Phe Ala Gln Ser Glu Pro Glu Leu Lys Leu Glu Ser
            20                  25                  30 gtg gtg att gtc agt cgt cat ggt gtg cgt gct cca acc aag gcc acg     144
Val Val Ile Val Ser Arg His Gly Val Arg Ala Pro Thr Lys Ala Thr
        35                  40                  45 caa ctg atg cag gat gtc acc cca gac gca tgg cca acc tgg ccg gta     192
Gln Leu Met Gln Asp Val Thr Pro Asp Ala Trp Pro Thr Trp Pro Val
    50                  55                  60 aaa ctg ggt tgg ctg aca ccg cgc ggt ggt gag cta atc gcc tat ctc     240
Lys Leu Gly Trp Leu Thr Pro Arg Gly Gly Glu Leu Ile Ala Tyr Leu
65                  70                  75                  80 gga cat tac caa cgc cag cgt ctg gta gcc gac gga ttg ctg gcg aaa     288
Gly His Tyr Gln Arg Gln Arg Leu Val Ala Asp Gly Leu Leu Ala Lys
                85                  90                  95 aag ggc tgc ccg cag tct ggt cag gtc gcg att att gct gat gtc gac     336
Lys Gly Cys Pro Gln Ser Gly Gln Val Ala Ile Ile Ala Asp Val Asp
            100                 105                 110 gag cgt acc cgt aaa aca ggc gaa gcc ttc gcc gcc ggg ctg gca cct     384
Glu Arg Thr Arg Lys Thr Gly Glu Ala Phe Ala Ala Gly Leu Ala Pro
        115                 120                 125 gac tgt gca ata acc gta cat acc cag gca gat acg tcc agt ccc gat     432
Asp Cys Ala Ile Thr Val His Thr Gln Ala Asp Thr Ser Ser Pro Asp
    130                 135                 140 ccg tta ttt aat cct cta aaa act ggc gtt tgc caa ctg gat aac gcg     480
Pro Leu Phe Asn Pro Leu Lys Thr Gly Val Cys Gln Leu Asp Asn Ala
145                 150                 155                 160 aac gtg act gac gcg atc ctc agc agg gca gga ggg tca att gct gac     528
Asn Val Thr Asp Ala Ile Leu Ser Arg Ala Gly Gly Ser Ile Ala Asp
                165                 170                 175 ttt acc ggg cat cgg caa acg gcg ttt cgc gaa ctg gaa cgg gtg ctt     576
Phe Thr Gly His Arg Gln Thr Ala Phe Arg Glu Leu Glu Arg Val Leu
            180                 185                 190 aat ttt ccg caa tca aac ttg tgc ctt aaa cgt gag aaa cag gac gaa     624
Asn Phe Pro Gln Ser Asn Leu Cys Leu Lys Arg Glu Lys Gln Asp Glu
        195                 200                 205 agc tgt tca tta acg cag gca tta cca tcg gaa ctc aag gtg agc gcc     672
Ser Cys Ser Leu Thr Gln Ala Leu Pro Ser Glu Leu Lys Val Ser Ala
    210                 215                 220 gac aat gtc tca tta acc ggt gcg gta agc ctc gca tca atg ctg acg     720
Asp Asn Val Ser Leu Thr Gly Ala Val Ser Leu Ala Ser Met Leu Thr
225                 230                 235                 240
```

```
gag ata ttt ctc ctg caa caa gca cag gga atg ccg gag ccg ggg tgg      768
Glu Ile Phe Leu Leu Gln Gln Ala Gln Gly Met Pro Glu Pro Gly Trp
            245                 250                 255 gga agg atc acc gat tca cac cag tgg aac acc ttg cta agt ttg cat      816
Gly Arg Ile Thr Asp Ser His Gln Trp Asn Thr Leu Leu Ser Leu His
        260                 265                 270 aac gcg caa ttt tat ttg cta caa cgc acg cca gag gtt gcc cgc agc      864
Asn Ala Gln Phe Tyr Leu Leu Gln Arg Thr Pro Glu Val Ala Arg Ser
    275                 280                 285 cgc gcc acc ccg tta tta gat ttg atc aag aca gcg ttg acg ccc cat      912
Arg Ala Thr Pro Leu Leu Asp Leu Ile Lys Thr Ala Leu Thr Pro His
290                 295                 300 cca ccg caa aaa cag gcg tat ggt gtg aca tta ccc act tca gtg ctg      960
Pro Pro Gln Lys Gln Ala Tyr Gly Val Thr Leu Pro Thr Ser Val Leu
305                 310                 315                 320 ttt atc gcc gga cac gat act aat ctg gca aat ctc ggc ggc gca ctg     1008
Phe Ile Ala Gly His Asp Thr Asn Leu Ala Asn Leu Gly Gly Ala Leu
            325                 330                 335 gag ctc aac tgg acg ctt ccc ggt cag ccg gat aac acg ccg cca ggt     1056
Glu Leu Asn Trp Thr Leu Pro Gly Gln Pro Asp Asn Thr Pro Pro Gly
        340                 345                 350 ggt gaa ctg gtg ttt gaa cgc tgg cgt cgg cta agc gat aac agc cag     1104
Gly Glu Leu Val Phe Glu Arg Trp Arg Arg Leu Ser Asp Asn Ser Gln
    355                 360                 365 tgg att cag gtt tcg ctg gtc ttc cag act tta cag cag atg cgt gat     1152
Trp Ile Gln Val Ser Leu Val Phe Gln Thr Leu Gln Gln Met Arg Asp
370                 375                 380 aaa acg ccg ctg tca tta aat acg ccc gga gag gtg aaa ctg acc         1200
Lys Thr Pro Leu Ser Leu Asn Thr Pro Gly Glu Val Lys Leu Thr
385                 390                 395                 400 ctg gca gga tgt gaa gag cga aat gcg cag ggc atg tgt tcg ttg gca     1248
Leu Ala Gly Cys Glu Glu Arg Asn Ala Gln Gly Met Cys Ser Leu Ala
            405                 410                 415 ggt ttt acg caa atc gtg aat gaa gca cgc ata ccg gcg tgc agt ttg     1296
Gly Phe Thr Gln Ile Val Asn Glu Ala Arg Ile Pro Ala Cys Ser Leu
        420                 425                 430 taa                                                                 1299
```

```
<210> SEQ ID NO 16
<211> LENGTH: 432
<212> TYPE: PRT
<213> ORGANISM: Escherichia coli
<220> FEATURE:
<223> OTHER INFORMATION: phytase protein

<400> SEQUENCE: 16

Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95

Lys Gly Cys Pro Gln Ser Gly Gln Val Ala Ile Ile Ala Asp Val Asp
            100                 105                 110
```

Glu Arg Thr Arg Lys Thr Gly Glu Ala Phe Ala Ala Gly Leu Ala Pro
            115                 120                 125

Asp Cys Ala Ile Thr Val His Thr Gln Ala Asp Thr Ser Ser Pro Asp
        130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
        195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
        275                 280                 285

Arg Ala Thr Pro Leu Leu Asp Leu Ile Lys Thr Ala Leu Thr Pro His
    290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Leu Ser Asp Asn Ser Gln
        355                 360                 365

Trp Ile Gln Val Ser Leu Val Phe Gln Thr Leu Gln Gln Met Arg Asp
370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

<210> SEQ ID NO 17
<211> LENGTH: 81
<212> TYPE: DNA
<213> ORGANISM: Methylophilus methylotrophus
<220> FEATURE:
<223> OTHER INFORMATION: gene encoding a signal sequence of methanol
      dehydrogenase
<220> FEATURE:
<221> NAME/KEY: CDS
<222> LOCATION: (1)..(81)

<400> SEQUENCE: 17 atg aaa ctg aaa tca tcc cgt gcc gtt gtt ggc gct ttg gtt ggg ggc     48
Met Lys Leu Lys Ser Ser Arg Ala Val Val Gly Ala Leu Val Gly Gly
1               5                   10                  15 ttg ttt gca agc att tcc ggc ctg gct gtg gca                         81

```
Leu Phe Ala Ser Ile Ser Gly Leu Ala Val Ala
            20                  25

<210> SEQ ID NO 18
<211> LENGTH: 27
<212> TYPE: PRT
<213> ORGANISM: Methylophilus methylotrophus
<220> FEATURE:
<223> OTHER INFORMATION: signal sequence of methanol dehydrogenase

<400> SEQUENCE: 18

Met Lys Leu Lys Ser Ser Arg Ala Val Val Gly Ala Leu Val Gly Gly
1               5                   10                  15

Leu Phe Ala Ser Ile Ser Gly Leu Ala Val Ala
            20                  25

<210> SEQ ID NO 19
<211> LENGTH: 66
<212> TYPE: DNA
<213> ORGANISM: Methylophilus methylotrophus
<220> FEATURE:
<223> OTHER INFORMATION: gene encoding a signal sequence of phytase
<220> FEATURE:
<221> NAME/KEY: CDS
<222> LOCATION: (1)..(66)

<400> SEQUENCE: 19 atg aaa gcg atc tta atc cca ttt tta tct ctt ctg att ccg tta acc     48
Met Lys Ala Ile Leu Ile Pro Phe Leu Ser Leu Leu Ile Pro Leu Thr
1               5                   10                  15 ccg caa tct gca ttc gct                                             66
Pro Gln Ser Ala Phe Ala
            20

<210> SEQ ID NO 20
<211> LENGTH: 22
<212> TYPE: PRT
<213> ORGANISM: Methylophilus methylotrophus
<220> FEATURE:
<223> OTHER INFORMATION: signal sequence of phytase

<400> SEQUENCE: 20

Met Lys Ala Ile Leu Ile Pro Phe Leu Ser Leu Leu Ile Pro Leu Thr
1               5                   10                  15

Pro Gln Ser Ala Phe Ala
            20

<210> SEQ ID NO 21
<211> LENGTH: 864
<212> TYPE: DNA
<213> ORGANISM: Methylophilus methylotrophus
<220> FEATURE:
<223> OTHER INFORMATION: promoter of sigma E gene

<400> SEQUENCE: 21
gatcaaaaac gatttggcat gcggatggta aaggcaggtg gggtgaaact gcacaaattc      60
caggttggct acccggcaac cggcccgcca tcccatcgca atcccgtcac cggtactgat     120
gtctgggttg gtggtatata agtagaccct gcctgcgccg cctgttgcca tcacggtgta     180
ttgtgcggag agagtaatca ccttgccgga ctggttgttg agcacatagg cgcccaggca     240
acggttgggg ccgtccgttg cggtctgctt gaagagttta tgcgtggtga tcagatcgac     300
tgcaatgtga tgttcaagga tggtgatatt cgggtgctcg cgcacacggt cggtcaaggt     360
tgtctgcacc gcttgtccgg tggcatcagc gacatgcacc acgcggcgat ggctatggcc     420
```

```
gccttcacgc gtcaggtgca ggcggtcatc ttcagcctcg cgggtaaaat taaccccttg      480
ctgtaataac cattcaatac tggcacggcc attggtgacc accatgcgcg tgacctcgct      540
gtcacataat ccagcgccgg catccaatgt atctttaata tgggcttcta ctgaatcctc      600
gttgttaaga actgcagcaa tccccccctg cgcccagttg ctggcactca tggttaattc      660
acgtttgctc agtatgcata ccctatgatt atctgccagg cgtaaggcca atgactggcc      720
tgccagacca ctgccaataa tcagcacatc gaacatttta ttcataggat ggtggggtca      780
atggaacttt gaagagatgt tcaggtcata tcaattgcca acattgctat ttgacattgt      840
aggcaaaaaa taagggatga gacg                                             864
```

```
<210> SEQ ID NO 22
<211> LENGTH: 1276
<212> TYPE: DNA
<213> ORGANISM: Methylophilus methylotrophus
<220> FEATURE:
<223> OTHER INFORMATION: promoter of ribosomal protein gene

<400> SEQUENCE: 22
gatctggcac aaacattgaa caattaggca gtctcccttt ccaaattaaa tcgtgtattg       60
gataaaatag cgtttgttac gcacagactg agcattttt ctgttaggta atcaatgggc       120
atattgaaca aacttccagg tggagtacgc taccccagcc ataaagaatg cagttatta       180 aaaaaactgc caaatggtg gctggtgggg acagtactgt tcgcagcccc tattgtgcat       240
gcctggtggc aagacggtga tttgctgacg catgatattg agcgtacctc catgtttctg       300
ggcctgctgt ttaccttctg gtttttttata ggcgcgatga tgattggcct gatagtgatc       360
attatcatga aagggccagg ctatgtatca gacccttatt acctacccaa ggaagacaaa       420
agcctggaga atccacccag agaggaataa gtgcttgatt gcaacatgaa atcagttta       480 taatcgcctt tttttcaacc ttgccacact ttgttcgtga cctttaagt gttttgacac       540 aaaaagggtt ggctctgaag gtggctttaa accacaagga atctcatgc gacactatga       600 aatcgtgttt attgttcacc ctgaccagag tgaacaagtg cctgcgatga ttgagcgtta       660
ccgcgcacaa atcacaggca atggcggcaa catccaccgt ctggaagact ggggccgccg       720
tcaacttgcc tacccaattc aaaaagtaca caaagcgcac tatgtgttga tgaacatcga       780
gtgcagccag gaagtgctgg aagagctgga gcatggcttc aaatttaacg atgctgtatt       840
acgtcacctg accatctcga ctaaaacagc cgtcacagca ccaagcccaa tgatgaaaga       900
ggaaaaatcc aaaaccatcg taggtgatgc acctgctgcg accactgagg cagctgctta       960
agggttgtga atacgctggt gattgcggca accattcact ctgttgaagc gttgcgttac      1020
acaccggcag gcttaccctt gttgcgattg caattgcaac atgattcaga acagcaagaa      1080
gccgggatga atcgcaaggt gcagtgtcag ttacccgcag tactgattgg tgaaaaagcc      1140
aatctgccat tgcaaagcgg cgatcaaatc aaagtaaaag ggttttttggc acaacgcagt      1200 gcaaagagca cacaggtggt actgcacata caagagttac agcgaataca gtattaaaga      1260
atttaaggag tttcaa                                                     1276
```

```
<210> SEQ ID NO 23
<211> LENGTH: 39
<212> TYPE: DNA
<213> ORGANISM: Artificial sequence
<220> FEATURE:
<223> OTHER INFORMATION: PCR primer
```

<400> SEQUENCE: 23

```
cccggatccg cacggatcac tgtattcggc tgcaacttt                                    39
```

<210> SEQ ID NO 24
<211> LENGTH: 40
<212> TYPE: DNA
<213> ORGANISM: Artificial sequence
<220> FEATURE:
<223> OTHER INFORMATION: PCR primer

<400> SEQUENCE: 24

```
cccggatccc cgtgttgcta ggatggttgt tcttggatca                                   40
```

<210> SEQ ID NO 25
<211> LENGTH: 750
<212> TYPE: DNA
<213> ORGANISM: Morganella morganii
<220> FEATURE:
<221> NAME/KEY: CDS
<222> LOCATION: (1)..(747)
<220> FEATURE:
<223> OTHER INFORMATION: gene encoding acid phosphatase

<400> SEQUENCE: 25

```
atg aag aag aat att atc gcc ggt tgt ctg ttc tca ctg ttt tcc ctt              48
Met Lys Lys Asn Ile Ile Ala Gly Cys Leu Phe Ser Leu Phe Ser Leu
1               5                   10                  15 tcc gcg ctg gcc gcg atc ccg gcg ggc aac gat gcc acc acc aag ccg              96
Ser Ala Leu Ala Ala Ile Pro Ala Gly Asn Asp Ala Thr Thr Lys Pro
            20                  25                  30 gat tta tat tat ctg aaa aat gaa cag gct atc gac agc ctg aaa ctg             144
Asp Leu Tyr Tyr Leu Lys Asn Glu Gln Ala Ile Asp Ser Leu Lys Leu
        35                  40                  45 tta ccg cca ccg ccg gaa gtc ggc agt att cag ttt tta aat gat cag             192
Leu Pro Pro Pro Pro Glu Val Gly Ser Ile Gln Phe Leu Asn Asp Gln
    50                  55                  60 gca atg tat gag aaa ggc cgt atg ctg cgc aat acc gag cgc gga aaa             240
Ala Met Tyr Glu Lys Gly Arg Met Leu Arg Asn Thr Glu Arg Gly Lys
65                  70                  75                  80 cag gca cag gca gat gct gac ctg gcc gca ggg ggt gtg gca acc gca             288
Gln Ala Gln Ala Asp Ala Asp Leu Ala Ala Gly Gly Val Ala Thr Ala
                85                  90                  95 ttt tca ggg gca ttc ggc tat ccg ata acc gaa aaa gac tct ccg gag             336
Phe Ser Gly Ala Phe Gly Tyr Pro Ile Thr Glu Lys Asp Ser Pro Glu
            100                 105                 110 ctg tat aaa ctg ctg acc aat atg att gag gat gcc ggt gat ctt gcc             384
Leu Tyr Lys Leu Leu Thr Asn Met Ile Glu Asp Ala Gly Asp Leu Ala
        115                 120                 125 acc cgc tcc gcc aaa gaa cat tac atg cgc atc cgg ccg ttt gcg ttt             432
Thr Arg Ser Ala Lys Glu His Tyr Met Arg Ile Arg Pro Phe Ala Phe
    130                 135                 140 tac ggc aca gaa acc tgt aat acc aaa gat cag aaa aaa ctc tcc acc             480
Tyr Gly Thr Glu Thr Cys Asn Thr Lys Asp Gln Lys Lys Leu Ser Thr
145                 150                 155                 160 aac gga tct tac ccg tca ggt cat acg tct atc ggc tgg gca acc gca             528
Asn Gly Ser Tyr Pro Ser Gly His Thr Ser Ile Gly Trp Ala Thr Ala
                165                 170                 175 ctg gtg ctg gcg gaa gtg aac ccg gca aat cag gat gcg att ctg gaa             576
Leu Val Leu Ala Glu Val Asn Pro Ala Asn Gln Asp Ala Ile Leu Glu
            180                 185                 190
```

```
cgg ggt tat cag ctc gga cag agc cgg gtg att tgc ggc tat cac tgg    624
Arg Gly Tyr Gln Leu Gly Gln Ser Arg Val Ile Cys Gly Tyr His Trp
            195                 200                 205 cag agt gat gtg gat gcc gcg cgg att gtc ggt tca gcc gct gtc gcg    672
Gln Ser Asp Val Asp Ala Ala Arg Ile Val Gly Ser Ala Ala Val Ala
        210                 215                 220 aca tta cat tcc gat ccg gca ttt cag gcg cag tta gcg aaa gcc aaa    720
Thr Leu His Ser Asp Pro Ala Phe Gln Ala Gln Leu Ala Lys Ala Lys
225                 230                 235                 240 cag gaa ttt gca caa aaa tca cag aaa taa                            750
Gln Glu Phe Ala Gln Lys Ser Gln Lys
                245
```

<210> SEQ ID NO 26
<211> LENGTH: 249
<212> TYPE: PRT
<213> ORGANISM: Morganella morganii
<220> FEATURE:
<223> OTHER INFORMATION: gene encoding acid phosphatase

<400> SEQUENCE: 26

```
Met Lys Lys Asn Ile Ile Ala Gly Cys Leu Phe Ser Leu Phe Ser Leu
1               5                   10                  15

Ser Ala Leu Ala Ala Ile Pro Ala Gly Asn Asp Ala Thr Thr Lys Pro
            20                  25                  30

Asp Leu Tyr Tyr Leu Lys Asn Glu Gln Ala Ile Asp Ser Leu Lys Leu
        35                  40                  45

Leu Pro Pro Pro Pro Glu Val Gly Ser Ile Gln Phe Leu Asn Asp Gln
    50                  55                  60

Ala Met Tyr Glu Lys Gly Arg Met Leu Arg Asn Thr Glu Arg Gly Lys
65                  70                  75                  80

Gln Ala Gln Ala Asp Ala Asp Leu Ala Ala Gly Gly Val Ala Thr Ala
                85                  90                  95

Phe Ser Gly Ala Phe Gly Tyr Pro Ile Thr Glu Lys Asp Ser Pro Glu
            100                 105                 110

Leu Tyr Lys Leu Leu Thr Asn Met Ile Glu Asp Ala Gly Asp Leu Ala
        115                 120                 125

Thr Arg Ser Ala Lys Glu His Tyr Met Arg Ile Arg Pro Phe Ala Phe
    130                 135                 140

Tyr Gly Thr Glu Thr Cys Asn Thr Lys Asp Gln Lys Lys Leu Ser Thr
145                 150                 155                 160

Asn Gly Ser Tyr Pro Ser Gly His Thr Ser Ile Gly Trp Ala Thr Ala
                165                 170                 175

Leu Val Leu Ala Glu Val Asn Pro Ala Asn Gln Asp Ala Ile Leu Glu
            180                 185                 190

Arg Gly Tyr Gln Leu Gly Gln Ser Arg Val Ile Cys Gly Tyr His Trp
        195                 200                 205

Gln Ser Asp Val Asp Ala Ala Arg Ile Val Gly Ser Ala Ala Val Ala
    210                 215                 220

Thr Leu His Ser Asp Pro Ala Phe Gln Ala Gln Leu Ala Lys Ala Lys
225                 230                 235                 240

Gln Glu Phe Ala Gln Lys Ser Gln Lys
                245
```

```
<210> SEQ ID NO 27
<211> LENGTH: 50
<212> TYPE: DNA
<213> ORGANISM: Artificial sequence
<220> FEATURE:
<223> OTHER INFORMATION: PCR primer

<400> SEQUENCE: 27
gcatttccgg cctggctgtg gcagcgatcc cggcgggcaa cgatgccacc            50

<210> SEQ ID NO 28
<211> LENGTH: 28
<212> TYPE: DNA
<213> ORGANISM: Artificial sequence
<220> FEATURE:
<223> OTHER INFORMATION: PCR primer

<400> SEQUENCE: 28
ttatttctgt gattttgtg caaattcc                                     28

<210> SEQ ID NO 29
<211> LENGTH: 35
<212> TYPE: DNA
<213> ORGANISM: Artificial sequence
<220> FEATURE:
<223> OTHER INFORMATION: PCR primer

<400> SEQUENCE: 29
tgccacagcc aggccggaaa tgcttgcaaa caagc                            35

<210> SEQ ID NO 30
<211> LENGTH: 39
<212> TYPE: DNA
<213> ORGANISM: Artificial sequence
<220> FEATURE:
<223> OTHER INFORMATION: PCR primer

<400> SEQUENCE: 30
ggcaagcttc tgttcctgca cctgcatggc atggcgcgc                        39

<210> SEQ ID NO 31
<211> LENGTH: 27
<212> TYPE: DNA
<213> ORGANISM: Artificial sequence
<220> FEATURE:
<223> OTHER INFORMATION: PCR primer

<400> SEQUENCE: 31
actttctccc aatctcttaa gaatgcg                                     27

<210> SEQ ID NO 32
<211> LENGTH: 46
<212> TYPE: DNA
<213> ORGANISM: Artificial sequence
<220> FEATURE:
<223> OTHER INFORMATION: PCR primer

<400> SEQUENCE: 32
ttcttaagag attgggagaa agtatgaaag cgatcttaat cccatt                46

<210> SEQ ID NO 33
<211> LENGTH: 32
<212> TYPE: DNA
<213> ORGANISM: Artificial sequence
<220> FEATURE:
<223> OTHER INFORMATION: PCR primer
```

<400> SEQUENCE: 33
ggcggtacca cagttcttcg tttgtcatca gc				32

<210> SEQ ID NO 34
<211> LENGTH: 51
<212> TYPE: DNA
<213> ORGANISM: Artificial sequence
<220> FEATURE:
<223> OTHER INFORMATION: PCR primer

<400> SEQUENCE: 34
ttcttaagag attgggagaa agtatgaaga agaatattat cgccggttgt c			51

<210> SEQ ID NO 35
<211> LENGTH: 45
<212> TYPE: DNA
<213> ORGANISM: Artificial sequence
<220> FEATURE:
<223> OTHER INFORMATION: PCR primer

<400> SEQUENCE: 35
agcttcagct ccggctcact ctgggccagc gcggaaaggg aaaac			45

<210> SEQ ID NO 36
<211> LENGTH: 33
<212> TYPE: DNA
<213> ORGANISM: Artificial sequence
<220> FEATURE:
<223> OTHER INFORMATION: PCR primer

<400> SEQUENCE: 36
ttggaattcc ccgttctgga taatgttttt tgc				33

<210> SEQ ID NO 37
<211> LENGTH: 26
<212> TYPE: DNA
<213> ORGANISM: Artificial sequence
<220> FEATURE:
<223> OTHER INFORMATION: PCR primer

<400> SEQUENCE: 37
tacgctcatc tcctttgcct gcaggg				26

<210> SEQ ID NO 38
<211> LENGTH: 46
<212> TYPE: DNA
<213> ORGANISM: Artificial sequence
<220> FEATURE:
<223> OTHER INFORMATION: PCR primer

<400> SEQUENCE: 38
tgcaggcaaa ggagatgagc gtaatgaaac tgaaatcatc ccgtgc			46

<210> SEQ ID NO 39
<211> LENGTH: 32
<212> TYPE: DNA
<213> ORGANISM: Artificial sequence
<220> FEATURE:
<223> OTHER INFORMATION: PCR primer

<400> SEQUENCE: 39
gccgaattca cagttcttcg tttgtcatca gc				32

METHOD FOR PRODUCING PROTEIN

CROSS-REFERENCE TO RELATED APPLICATIONS

The present application is a continuation of PCT/JP06/309598, filed on May 12, 2006, and which claims priority to JP 2005-139798, filed on May 12, 2005, all of which are incorporated herein by reference.

TECHNICAL FIELD

The present invention relates to a method of secretory production of a protein including industrially useful enzymes and biologically active proteins by using methanol-assimilating bacteria.

BACKGROUND ART

Methanol is a fermentative material that is available in a large amount at a low cost and is very useful as a carbon source. There have been developed a method of producing an L-amino acid by a methanol-assimilating bacterium using methanol as a major carbon source (Patent Document 1) and a method of producing a polysaccharide using a methanol-assimilating bacterium (Patent Document 2).

Also, there have been known an example of production of lacZ in bacterial cells using a promoter of an alcohol oxidase (AOX) gene by induction with methanol in *Pichia* yeast (Non-Patent Document 1) and an example of secretion of aprotinin (bovine-derived pancreatic trypsin inhibitor) as an active form in a culture supernatant (Non-Patent Document 2).

Further, there has been known an example of accumulation of a fluorescent protein (GFP) in a cell of a non-obligate methanol-assimilating bacterium, *Methylobacterium extorquens*, which is one of methanol-assimilating bacteria (Patent Document 3 and Non-Patent Document 3). However, there has not been known an example of secretion of a protein out of cells of an obligate methanol-assimilating bacterium.

Patent Document 1: EP 1,188,822
Patent Document 2: JP 11-56384 A
Patent Document 3: WO 2003/046226 A1
Non-patent Document 1: Nucleic Acids Res. 1987 May 11; 15(9):3859-76.
Non-patent Document 2: J Ind Microbiol. 1991 April; 7(3): 197-201.
Non-patent Document 3: FEMS Microbiol Lett. 2000 Dec. 15; 193(2):195-200

DISCLOSURE OF THE INVENTION

It is an object of the present invention to provide a method of efficient secretory production of a protein that is difficult to be secretory produced by using an *Escherichia coli* or the like.

The inventors of the present invention have paid an attention to a promoter and a signal sequence which are derived from a methanol-assimilating bacterium and have made extensive studies. As a result, they have found that secretory production of a protein can be efficiently performed by culturing a methanol-assimilating bacterium, which harbors a DNA construct containing a promoter sequence which functions in the methanol-assimilating bacterium and a nucleotide sequence encoding a signal sequence and a target protein, in a liquid medium containing methanol as a major carbon source, thus accomplished the present invention.

That is, the present invention is as follows.

(1) A method of producing a protein, comprising culturing a methanol-assimilating bacterium in a liquid medium containing methanol as a major carbon source to allow the bacterium to secrete the target protein, and recovering the secreted target protein, wherein said bacterium harbors a DNA construct which contains a promoter sequence that functions in the methanol-assimilating bacterium and a nucleotide sequence that encodes a polypeptide containing a signal sequence and a target protein which is functionally connected to the promoter sequence.

(2) The method according to (1), wherein the promoter sequence which functions in the methanol-assimilating bacterium is selected from the group consisting of a methanol dehydrogenase promoter, a tac promoter, a σE promoter, and a ribosomal protein promoter.

(3) The method according to (1), wherein the promoter sequence is a nucleotide sequence of SEQ ID NO: 11, 12, 21, or 22.

(4) The method according to any one of (1) to (3), wherein the signal sequence is a signal sequence of a protein selected from methanol dehydrogenase, phytase, and acid phosphatase.

(5) The method according to any one of (1) to (3), wherein the signal sequence has an amino acid sequence selected from SEQ ID NO: 18 and SEQ ID NO: 20.

(6) The method according to any one of (1) to (5), wherein the methanol-assimilating bacterium belongs to the genus selected from the group consisting of *Methylophilus*, *Methylobacillus*, *Methylophaga*, *Achromobacter*, *Pseudomonas*, *Protaminobacter*, *Methanomonas*, *Microcyclus*, and *Methylobacterium*.

(7) The method according to any one of (1) to (6), wherein the protein is selected from the group consisting of phytase, interleukin, transglutaminase, interferon, insulin, acid phosphatase, and peptide synthase.

(8) The method according to any one of (1) to (7), wherein the methanol-assimilating bacterium is an obligate methanol-assimilating bacterium.

(9) The method according to (8), wherein the obligate methanol-assimilating bacterium belongs to the genus selected from the group consisting of *Methylophilus*, *Methylobacillus*, and *Methylophaga*.

DESCRIPTION OF THE PREFERRED EMBODIMENTS

The production method of the present invention comprises culturing a methanol-assimilating bacterium harboring a DNA construct containing a promoter sequence that functions in the methanol-assimilating bacterium and a nucleotide sequence that encodes a polypeptide containing a signal sequence and a target protein sequence which is functionally connected to the promoter sequence, in a liquid medium containing methanol as a major carbon source to allow the bacterium to secrete the target protein; and recovering the secreted target protein. Herein, the term "secrete" refers to excretion or release of a target protein out of the bacterial cells and does not encompass accumulation of the target protein within cells.

That is, the methanol-assimilating bacterium produces a polypeptide containing a signal sequence and a target protein, and the target protein is transferred to a periplasm upon cleavage of the signal sequence, then being secreted out of the bacterial cells. The secreted protein is recovered, thereby the target protein is produced. Hereinafter, production of a protein by allowing a bacterium to secrete the protein and recovering the protein is referred to as "secretory production of a protein".

It is generally known that a secretory protein is translated as a prepeptide or a prepropeptide and is converted into a mature protein. That is, it is generally known that a secretory protein is translated as a prepeptide or a prepropeptide and is converted into a mature peptide or a propeptide upon cleavage of the pre-domain, and the propeptide is further converted into a mature protein upon cleavage of the pro-domain with a protease. Such a protease that cleaves a signal peptide is generally referred to as signal peptidase.

In the present invention, the target protein may be secreted as a mature protein or a propeptide, and when the target protein is secreted as a propeptide, the propeptide may be converted into a mature protein by treating the propeptide with an appropriate protease after recovery.

In this description, the term "signal sequence" refers to a sequence that is present in the N-terminal of a precursor type of a secretory protein and is recognized when the protein is secreted, and the term "signal peptide" refers to a peptide consisting of such amino acid residues.

In this description, a protein having both a pre-sequence and a pro-domain, that is, a primary translated product may be referred to as "prepro-protein", while a protein having no pre-sequence but having a pro-domain may be referred to as "pro-protein". The pro-domain of a pro-protein may be referred to as "pro-structure domain" or simply as "pro-structure", and in this description, the term "pro-structure domain/pro-structure" of a protein is used interchangeably with the term "pro-domain" of a protein.

A bacterium to be used in the production method of the present invention can be obtained by introducing a DNA construct which contains a promoter sequence that functions in a methanol-assimilating bacterium and a nucleotide sequence that encodes a polypeptide containing a signal sequence and a target protein sequence which is functionally connected to the promoter sequence, into a methanol-assimilating bacterium.

Herein, the term "methanol-assimilating bacterium" refers to a bacterium that can grow in a medium containing methanol as a main carbon source, and examples thereof include bacteria belonging to the genera *Methylophilus, Methylobacillus, Methylophaga, Achromobacter, Pseudomonas* (JP 45-25273 A), Protaminobacter (JP 49-125590 B), Methanomonas (JP 50-25790 A), *Microcyclus* (JP 52-18886 A), and *Methylobacterium*. Among them, preferable is an obligate methanol-assimilating bacterium that cannot grow or can slightly grow in a medium containing glucose as a single carbon source. Specific examples of such a bacterium that can grow in a medium containing methanol as a carbon source but cannot grow or can slightly grow in a medium containing glucose as a single carbon source include *Methylophilus* bacteria, *Methylobacillus* bacteria, and *Methylophaga* bacteria. An example of the *Methylophilus* bacterium includes *Methylophilus methylotrophus*, and examples of the *Methylobacillus* bacterium include *Methylobacillus glycogenes* and *Methylobacillus flagellatus*, and examples of the *Methylophaga* bacterium include *Methylophaga thalassica, Methylophaga marina*, and *Methylophaga alcaliphila* (Biology of Methylotrophus; Edited by Israel Goldberg and J. Stefan Roken and published by Butterworth-Heinemann). In addition, bacteria having a function to secrete methanol dehydrogenase (MDH) out of bacterial cells are also preferable.

Examples of *Methylophilus methylotrophus* include AS1 strain (NCIMB 10515), W3A1 (NCIMB 11348 strain), and ATCC 53528 strain. *Methylophilus methylotrophus* AS1 strain (NCIMB 10515) and W3A1 (NCIMB 11348 strain) are available from National Collections of Industrial and Marine Bacteria, address: NCIMB Lts., Torry Research Station 135, Abbey Road, Aberdeen AB9 8DG, United Kingdom).

Examples of *Methylobacillus glycogenes* include T-11 strain (NCIMB 11375), ATCC 21276 strain, ATCC 21371 strain, ATCC 29475 strain, ATR80 strain (described in Appl. Microbiol. Biotechnol., (1994), vol. 42, p 67-72), and A513 strain described in Appl. Microbiol. Biotechnol., (1994), vol. 42, p 67-72). *Methylobacillus glycogenes* NCIMB 11375 strain is available from National Collections of Industrial and Marine Bacteria (address: NCIMB Lts., Torry Research Station 135, Abbey Road, Aberdeen AB9 8DG, United Kingdom).

Examples of *Methylobacillus flagellatus* include ATCC 51484 strain, KT strain (described in N. I. Govorukhina et al., Microbiology (Russia) 56 (1987), pp. 849-854), and VKM B-1610 strain. *Methylobacillus flagellatus* VKM B-1610 strain is available from ALL-RUSSIAN COLLECTION OF MICROORGANISMS (Russia, 142290, Moscow Region, Pushchino, pr. Nauki, 5, IBPM).

*Methylophilus methylotrophus* ATCC 53528 strain, *Methylobacillus glycogenes* ATCC 21276 strain, ATCC 21371 strain, ATCC 29475 strain, *Methylobacillus flagellatus* ATTC 51484 strain can be obtained from the American Type Culture Collection (ATCC) (address: P.O. Box 1549, Manassas, Va. 20108, 1, United States of America).

Examples of *Methylophaga thalassica* include ATTC 33145 strain and ATTC 33146 strain. An example of *Methylophaga marina* includes ATCC 35842 strain. Am example of *Methylophaga alcaliphila* includes ATCCBAA-297™. *Methylophaga thalassica* ATTC 33145 strain and ATTC 33146 strain can be obtained from the American Type Culture Collection (ATCC) (address: P.O. Box 1549, Manassas, Va. 20108, 1, United States of America).

The term "promoter that functions in a methanol-assimilating bacterium", which is contained in a DNA construct to be introduced into the methanol-assimilating bacterium, refers to a promoter having promoter activity in the methanol-assimilating bacterium, but the promoter is not limited to one derived from a methanol-assimilating bacterium and may be derived from another microorganism. In addition, "promoter that functions in a methanol-assimilating bacterium" includes both a methanol-inducible promoter and a non-inducible promoter. Examples of the methanol-inducible promoter include a promoter of a methanol dehydrogenase gene, a promoter of a dihydroxyacetone synthase gene, and a promoter of a formate dehydrogenase gene.

Specific examples of the promoter that functions in a methanol-assimilating bacterium include, but not limited to, a methanol-inducible promoter of a methanol dehydrogenase gene (SEQ ID NO: 11), tac promoter which is a high-expression promoter derived from *Escherichia coli* (SEQ ID NO: 12), σE promoter (SEQ ID NO: 21), and ribosomal protein promoter (SEQ ID NO: 22).

Also, the promoter sequence is not limited to a wild-type promoter and may be a promoter obtained by modifying a wild-type sequence so that a desired gene is highly expressed. For example, the sequence may be obtained by modifying the wild-type promoter sequence so as to have a substitution, deletion, addition, or insertion of several nucleotides as long as the promoter has promoter activity in the above-mentioned bacteria. In addition, in order to increase the promoter activity, the promoter may be modified at -35 region or -10 region, or modified by adjusting the length of a spacer region between the -35 region and the -10 region. Examples of the method of modifying the -35 and -10 regions include the method described in EP 1,033,407 and the method described in Nucleic Acids Res. 1999 Dec. 15; 27(24): 4768-74.

The promoter activity is defined by the frequency of initiation of RNA synthesis. Examples of a method of evaluating the promoter activity and examples of strong promoters that can be used in the present invention are described in Goldstein et al. (Prokaryotic promoters in biotechnology. Biotechnol. Annu. Rev., 1995, 1, 105-128) or the like. In addition, as disclosed in WO 00/18935, the promoter may be modified to be stronger by introducing a nucleotide substitution of several nucleotides into the promoter region of an objective gene.

In a DNA construct to be introduced in a methanol-assimilating bacterium, a nucleotide sequence encoding a polypeptide containing a signal sequence and a target protein is functionally connected downstream of a promoter.

The "signal sequence which functions in a methanol-assimilating bacterium" means a sequence that can be recognized by the methanol-assimilating bacterium so as to secrete a target protein when it is connected to the target protein.

The signal sequence may be derived from a protein different from a target protein or contained in a precursor protein of a target protein. However, the signal sequence is preferably derived from a secretory protein of a host methanol-assimilating bacterium to be used. A signal sequence that can be used for the present invention may contain a part of an N-terminal side amino acid sequence of a target protein together with the signal sequence in a precursor protein from which the signal sequence is derived.

When the origin of a signal sequence is different from that of a target protein, a prepro-protein may be referred to as "heterologous fusion prepro-protein". For example, when the protein is insulin, it is referred to as "heterologous fusion prepro-insulin" in contradistinction to "prepro-insulin" or "pro-insulin".

The signal sequence is not particularly limited as long as it functions in a methanol-assimilating bacterium, and there may be used a signal sequence derived from a protein secreted from a methanol-assimilating bacterium or a signal sequence derived from a protein secreted from other bacteria, yeasts, plants, animals, etc. A specific example of the signal sequence includes a signal sequence of methanol dehydrogenase (MDH) that is derived from *Methylophilus methylotrophus* (amino acid sequence of SEQ ID NO: 18). Also, examples of a signal sequence derived from another bacterium include a signal sequence of phytase encoded by an appA gene of *Escherichia coli* (amino acid sequence of SEQ ID NO: 20) and a signal sequence of acid phosphatase of *Morganella morganii* (positions 1 to 20 of SEQ ID NO: 26). The nucleotide sequences encoding these amino acid sequences are shown in SEQ ID NOs: 17, 19, and 25, respectively.

A nucleotide sequence encoding a signal sequence may be a nucleotide sequence encoding a wild-type signal sequence, or a nucleotide sequence encoding a wild-type signal sequence may be substituted so that the codons are suitably used by a methanol-assimilating bacterium that secretes and produces a protein.

The "target protein" that can be secreted and recovered by the method of the present invention is not particularly limited as long as it can be secreted by using a methanol-assimilating bacterium when it is connected to the signal sequence that functions in the methanol-assimilating bacterium, and it includes various proteins such as secretory proteins and intracellular proteins derived from animals, plants, and microorganisms. The method of the present invention may be applied to a protein that cannot be obtained by secretory production in a gram-negative bacterium such as an *Escherichia* bacterium.

The "target protein" is preferably a heterologous protein that is derived from an origin different from a host methanol-assimilating bacterium.

When the "target protein" is itself a secreted protein, a protein having a sequence obtained by removing a pre-sequence and a pro-sequence from a precursor or a protein having a pro-sequence may be used. However, the "target protein" may be a protein obtained by removing at least one amino acid that constitutes a pre-domain and a pro-domain by cleaving a peptide bond from a precursor protein, and the target protein includes a protein having an N-terminal region that completely corresponds to that of a natural mature protein, a protein having at least one extra amino acid derived from a pre-domain or a pro-domain at the N-terminal as compared with a natural mature protein, and a protein having an amino acid sequence shorter than that of a natural mature protein.

The target protein to which the production method of the present invention can be applied is not particularly limited, and examples thereof include mature proteins or pro-proteins of the following proteins:

Phytase [EC: 3.1.3.2 3.1.3.26]
Human Interleukin 2 (IL2: Genbank Accession No. AAK26665, mature type IL2: amino acids at position 21 to 153)
Protein glutaminase
Trans glutaminase (Genbank Accession No. AF531437)
Interferon
Insulin (JP 07-284394 A)
Acidic phosphatase
Peptide synthetase (WO 2004/011653, WO 2004/065610)
Granulocyte stimulating factor (GCSF)

Among them, preferable are phytase and acid phosphatase produced in the Examples shown below.

Phytase (also referred to as phosphoanhydride phosphorylase) is an enzyme that hydrolyses phytin (also referred to as inositol hexakisphosphate or phytic acid) and is useful in the fields of food, agriculture, and medical etc. The followings can be used as phytase. The information on the amino acid sequence of each phytase and the nucleotide sequence encoding each phytase can be obtained by referring to Genbank Accession No. of each phytase.

Phytase derived from *Escherichia coli*: Genbank Accession No. AAC74065 (SEQ ID NO: 16), the mature protein: amino acids at positions 23 to 432
Phytase derived from mold: Genbank Accession No. AAU93518, AAU93517, and AAG40885, and BAB40715
Phytase derived from *Bacillus*: Genbank Accession No. AAC38573, AAG 17903, and AAL 59320
Phytase derived from yeast: Genbank Accession No. CAB70441
Phytase derived from *Yersinia*: Genbank Accession No. YP_070934
Phytase derived from *Klebsiella*: Genbank Accession No. AAM23271
Phytase derived from *Xanthomonas*: Genbank Accession No. AAM38967
Phytase derived from *Pseudomonas*: Genbank Accession No. AAN77879
Phytase derived from mushroom: Genbank Accession No. CAC48195, CAC48164, and CAC48234
Phytase derived from maize: Genbank Accession No. AAB52233
Phytase derived from soybean: Genbank Accession No. AAK49438
Phytase derived from sweetpotate: Genbank Accession No. AAF60315

Phytase derived from rat: Genbank Accession No. AAA42305

Acid phosphatase is an enzyme that catalyzes a reaction of hydrolyzing a phosphate under acidic conditions (EC 3.1.3.2), and it is possible to use the following acid phosphatase derived from *Morganella morganii*, acid phosphatase described in WO 96/37603, and mutants thereof.

Acid phosphatase derived from *Morganella morganii*: Genbank Accession No. AB035805 (SEQ ID NO: 25) mature type: amino acids at position 21 to 259

A gene encoding each of these proteins may be modified depending on a host to be used and/or to achieve a desired activity, and such modification includes modification to add, delete, or substitute at least one amino acid in the amino acid sequence to be encoded. Such a general molecular biological technology including modification methods, gene cloning methods, and detection methods of the produced proteins are well known to those skilled in the art. For example, the technologies are described in Sambrook et al., 2001, Molecular Cloning: A Laboratory Manual, Third Edition (1989) Cold Spring Harbor Laboratory Press, Cold Spring Harbor, N.Y., DNA cloning: A Practical Approach, Volumes I and II (D. N. Glover ed. 1985), F. M. Ausubel et al. (eds), Current Protocols in Molecular Biology, John Wiley & Sons, Inc. (1994), PCR Technology: Principles and Application for DNA Amplification, H. Erlich, ed., Stockton Pres, etc. In the case of heterologous proteins, a gene may be modified to have substitution of codons so that the codons are frequently used in a microorganism for secretory production.

A gene encoding a protein can be obtained by PCR or the like using primers designed based on a known sequence. Also, there may be used a gene encoding a target protein obtained by isolating from chromosomes of microorganisms, animals, plants, etc. by hybridization or the like based on homology and a gene whose nucleotide sequence has been determined. Alternatively, a gene obtained by chemical synthesis based on a known nucleotide sequence may be used. The sequence information is available from a database such as Genbank.

In addition, the target protein may be a protein having substitution, deletion, insertion, or addition of one or several amino acids at one or a plurality of positions as long as it has activity of the target protein. In the present invention, depending on the position of amino acid residues in the tertiary structure or types of a protein, the term "one or several" specifically means 1 to 30, preferably 1 to 20, and more preferably 1 to 10.

The above-mentioned substitution in a protein is conservative substitution which maintains the protein activity. The substitution is a change to remove at least one residue in an amino acid sequence and to insert another residue thereto. Examples of such a substitution of an amino acid that is performed to substitute an original amino acid of an enzyme protein and is considered as a conservative substitution include: substitution of Ser or Thr for Ala; substitution of Gln, His, or Lys for Arg; substitution of Glu, Gln, Lys, His, or Asp for Asn; substitution of Asn, Glu, or Gln for Asp; substitution of Ser or Ala for Cys; substitution of Asn, Glu, Lys, His, Asp, or Arg for Gln; substitution of Gly, Asn, Gln, Lys, or Asp for Glu; substitution of Pro for Gly; substitution of Asn, Lys, Gln, Arg, or Tyr for His; substitution of Leu, Met, Val, or Phe for Ile; substitution of Ile, Met, Val, or Phe for Leu; substitution of Asn, Glu, Gln, His, or Arg for Lys; substitution of Ile, Leu, Val, or Phe for Met; substitution of Trp, Tyr, Met, Ile, or Leu for Phe; substitution of Thr or Ala for Ser; substitution of Ser or Ala for Thr; substitution of Phe or Tyr for Trp; substitution of His, Phe, or Trp for Tyr; and substitution of Met, Ile, or Leu for Val.

A DNA encoding a protein substantially identical to the above-mentioned protein can be obtained by modifying a nucleotide sequence encoding such an enzyme, for example, by a site-specific mutation, so that an amino acid residue at a specific site is substituted, deleted, inserted, added, or inverted. Moreover, the above-mentioned modified DNA can be obtained by a conventionally known mutation treatment. Examples of the mutation treatment include a method of treating an unmutated DNA in vitro with hydroxylamine or the like, a method of treating a microorganism harboring an unmutated DNA, for example, an *Escherichia* bacterium, with irradiation of ultraviolet ray or with a mutagen that is generally used for a mutation treatment such as N-methyl-N'-nitro-N-nitrosoguanidine (NTG) or nitrous acid, a method of artificially causing a random error by converting a component ratio of deoxynucleotides in a PCR reaction solution from equal rates (general) to unequal rates, that is, an error-prone PCR.

A DNA encoding a substantially identical protein can be obtained by expressing a DNA having such a mutation in an appropriate cell and determining the activity of the product expressed from the DNA.

Also, a DNA that hybridizes with a nucleotide sequence complementary to that of a wild-type gene or with a probe having a part thereof under stringent conditions and encodes a protein having a target protein activity can be obtained from a DNA encoding a mutated protein or cells containing the DNA. Herein, the term "stringent conditions" refers to conditions where a so-called specific hybrid is formed and non-specific hybrid is not formed. It is difficult to clearly define the conditions with numerical value, but examples thereof for hybridization include: conditions where DNAs with high homology, for example, DNAs having homology of not less than 70%, preferably homology of not less than 80%, more preferably homology of not less than 90%, particularly preferably homology of not less than 95% hybridize with each other and DNAs with homology less than 70% do not hybridize with each other; and conditions for washing in general Southern hybridization, i.e., conditions for washing at temperature of 60° C. and with salt concentrations of 1×SSC, 0.1% SDS, preferably 0.1×SSC, 0.1% SDS.

The above mentioned target protein may be directly connected to a signal sequence or indirectly connected to a signal sequence via a linker sequence. In the case of including a linker sequence, the linker sequence may be any sequence as long as it does not inhibit productivity of a polypeptide or activity of a target protein, and for example, a sequence for purifying a target protein such as polyhistidine may be used.

A nucleotide sequence encoding a polypeptide containing a signal sequence and a target protein may be appropriately prepared by connecting a nucleotide sequence encoding a signal sequence to a nucleotide sequence encoding a target protein with a restriction enzyme or the like.

In addition, in the case of using a signal sequence and a target protein that are derived from the same precursor protein, a sequence encoding a precursor protein including a signal sequence and a target protein may be amplified by PCR or the like. Various known modified PCR methods may be used, and among them, crossover PCR is advantageously used for the amplification.

A DNA construct to be introduced into a methanol-assimilating bacterium can be prepared by functionally connecting a nucleotide sequence encoding a polypeptide containing a signal sequence and a target protein to a promoter. The phrase "functionally connecting a nucleotide sequence which encodes a polypeptide containing a signal sequence and a target protein to a promoter" means that mRNA encoding a polypeptide is transcribed by a promoter so that the polypeptide is produced by the bacterium when the construct is introduced into the bacterium.

The nucleotide sequence is preferably connected to a promoter comprising a 5'-untranslated region including a transcription initiation site in the region upstream of a translation initiation codon in a sequence encoding a polypeptide. The 5'-untranslated region may be a 5'-untranslated region of a sequence from which a promoter is derived such as a 5'-untranslated region of an MDH gene in the case of an MDH gene promoter. In addition, the 5'-untranslated region may be a 5'-untranslated region of a gene from which a sequence encoding a signal sequence is derived such as a 5'-untranslated region of a phytase gene in the case of using a signal sequence of phytase.

It is known that translation efficiency of mRNA is significantly affected by substitution of several nucleotides in a spacer between a ribosome binding site (RBS) and an initiation codon, in particular, in a sequence just upstream of the initiation codon, and therefore a 5'-untranslated region including such modification may be used when the construct includes the 5'-untranslated region.

Operations for obtaining such a DNA construct may be performed by using a gram-negative bacterium that is easily genetically modified, such as an *Escherichia* bacterium, or by using a microorganism that secretes a protein.

In order to modify a methanol-assimilating bacterium so as to harbor the above-mentioned DNA construct, for example, a vector carrying the DNA construct may be introduced. For example, a host methanol-assimilating bacterium may be transformed by: preparing a recombinant DNA by connecting a gene fragment encoding the protein to a vector that functions in a methanol-assimilating bacterium, preferably to a multi-copy vector; and introducing the recombinant DNA.

A promoter, signal sequence, protein sequence can be obtained by, for example, PCR (polymerase chain reaction; White, T. J. et al., Trends Genet. 5, 185 (1989)) using a chromosomal DNA of an animal, plant, or microorganism having an objective sequence as a template. The chromosomal DNA may be prepared from a bacterium that serves as a DNA donor, for example, by the method of Saito and Miura (H. Saito and K. Miura, Biochem. Biophys. Acta, 72, 619 (1963), Experiment Manual for Biotechnology, edited by The Society for Biotechnology, Japan, p. 97-98, Baifukan Co., Ltd., 1992) or the like. PCR primers can be prepared based on gene sequences registered in known database such as Genbank or based on information on a region conserved between genes having known sequences in another bacterium or the like.

Examples of a vector capable of autonomously replicating in a methanol-assimilating bacterium include plasmids capable of autonomously replicating in, for example, a *Methylophilus* or *Methylobacillus* bacterium. Specific examples thereof include a broad-host-range vector RSF1010 and a derivative thereof, such as pAYC32 (Chistoserdov, A. Y., Tsygankov, Y. D. Plasmid, 1986, 16, 161-167), pMFY42 (gene, 44, 53 (1990)), pRP301, or pTB70 (Nature, 287, 396, (1980)).

Also, pAYCTER3 used in Examples of this description is a preferable vector. The pAYCTEP3 is a plasmid obtained by deleting upstream region of a streptomycin-resistant gene of pAYC32 (strA and strB) and inserting therein a multi-cloning site of pUC19 and a terminator of an rmB gene of *E. coli*. That is, the pAYCTER3 is a high-expression vector that dose not express resistance to streptomycin but becomes resistant to streptomycin when a DNA containing a promoter sequence is inserted into the multi-cloning site in a forward direction with respect to strA.

In order to prepare a recombinant DNA by connecting the DNA construct to a vector which carries a marker that functions in a methanol-assimilating bacterium, a vector is cleaved with a restriction enzyme suitable for the end of a target gene. The ligation is generally performed with a ligase such as T4 DNA ligase.

Introduction of a recombinant DNA prepared as described above into a methanol-assimilating bacterium may be performed by transformation methods which have been reported. Examples thereof include a method comprising preparing a competent cell from a cell at the proliferation stage and introducing a DNA thereinto (Dubunau and Davidoff-Abelson, J. Mol. Biol., 56, 209 (1971); Duncan, C. H., Wilson, G. A and Young, F. E, Gene, 1, 153 (1977)) and a method comprising converting a host cell into a protoplast or spheroplast that easily receives a recombinant DNA and introducing a recombinant DNA into the DNA recipient bacterium (Chang, S, and Choen, S. N., Molec. Gen. Genet., 168, 111 (1979)).

In addition, a methanol-assimilating bacterium having a DNA construct of the present invention can be constructed by introducing one copy or multiple copies of a DNA construct on a chromosomal DNA of a methanol-assimilating bacterium. One copy or multiple copies of a DNA construct of the present invention can be introduced on a chromosomal DNA of a methanol-assimilating bacterium by homologous recombination using a sequence that is present on a chromosomal DNA in multiple copies as a target or by random insertion to a chromosomal DNA using a phage or the like. As a sequence present on a chromosomal DNA in multiple copies, a transposon, a repetitive sequence, an inverted repeat present at the end of a transposable element, or the like can be used. In addition, amplification with a vector and multicopying on chromosome may be combined with the above-mentioned modification of an expression regulation sequence.

A protein can be produced by culturing a methanol-assimilating bacterium obtained as described above in a liquid medium containing methanol as a carbon source to allow the bacterium to secrete the target protein and then recovering the secreted target protein.

In this description, the "secretion" of a protein or a peptide means transport of a protein or peptide molecule out of bacterial cells, which includes not only a case where the protein or peptide eventually becomes completely free in a medium but also a case where a part thereof is present in the outside of the bacterial cells as well as a case where the protein or peptide is present in the surface layer of the bacterial cells.

In the present invention, a target protein is preferably secreted to such an extent that it is collected from a medium or bacterial cells.

The methanol-assimilating bacterium is cultured in a medium containing methanol as a carbon source. Examples of the medium containing methanol as a carbon source include a medium supplemented with 0.001 to 30% methanol. The medium may contain a carbon source other than methanol, such as: sugars including glucose, sucrose, lactose, galactose, fructose, and a starch hydrolysate; alcohols such as glycerol and sorbitol; and organic acids such as fumaric acid, citric acid, and succinic acid.

As a medium component other than methanol, a nitrogen source or an inorganic ion that is used in general culture may be added. In order to achieve higher growth, an organic trace nutrient such as a vitamin and an amino acid may be added, if necessary. As the nitrogen source, ammonia gas, ammonia water, ammonium salts, etc. may be used. As the inorganic ion, calcium ion, magnesium ion, phosphate ion, potassium ion, iron ion, etc. may be appropriately used, if necessary. For example, culture may be performed at pH 5.0 to 9.0 and 15° C. to 45° C. under aerobic conditions, and a culture period may be about 1 to 7 days. When a methanol-assimilating bacterium is cultured under such conditions, a target protein is produced in a large amount in bacterial cells and then efficiently secreted.

In a case of using a methanol-inducible promoter such as an MDH gene promoter, culture may be performed under inducible conditions to increase production of a polypeptide. Induction may be performed according to conditions generally used for inducing an MDH gene promoter. In general, when a methanol-assimilating bacterium is cultured in methanol, an MDH promoter can function without requiring particular induction.

A protein secreted in a medium by the method of the present invention can be separated and purified from the medium after culture in accordance with a method that is well known to a person skilled in the art. For example, the protein can be separated and purified by: removing bacterial cells by centrifugation or the like; and performing a known appropriate method such as desalting, ethanol precipitation, ultrafiltration, gel-filtration chromatography, ion-exchange column chromatography, affinity chromatography, middle or high-pressure liquid chromatography, reverse-phase chromatography, or hydrophobic chromatography; or combination of these methods. When a polypeptide comprises a sequence for purification, purification can be performed using the sequence.

A protein secreted in the surface layer of bacterial cells by the method of the present invention can be separated and purified by: solubilizing the protein by a method known to a person skilled in the art, for example, by increasing the salt content, using a surfactant, etc.; and performing the same procedures as in the case where the protein is secreted in a medium. Also, in some cases, the protein secreted in the surface layer of bacterial cells may be used as, for example, an immobilized enzyme without solubilizing the protein.

EXAMPLES

The present invention will be described in more detail with the following examples, but is not limited thereto in any sense.

Example 1

Secretory Expression of Beta-Lactamase Derived from *Escherichia coli* K-12 Strain in *Methylophilus methylotrophus* ATCC 53528

(1) Construction of an Expression Plasmid that Functions in Methanol-Assimilating Bacterium, pAYCTER3

The synthetic DNAs shown in SEQ ID NOS: 3 and 4 which was designed to contain the sequence of the multi-cloning site of pUC19 were annealed by a known method to prepare a polylinker. The polylinker was designed to have the same end shapes as those obtained by cleaving with restriction enzymes EcoRI and BglII. Further, the primers shown in SEQ ID NOS: 5 and 6 were synthesized, and the region encoding the terminator sequence of rrnB was amplified by PCR with chromosomal DNA of *Escherichia coli* K-12 prepared by the conventional method (method of Saito and Miura [Biochim. Biophys. Acta, 72, 619 (1963)]). A sequence recognized by the restriction enzyme BglII was introduced into the primer of SEQ ID NO: 3, and a sequence recognized by restriction enzyme BclI was introduced into the primer of SEQ ID NO: 4. PCR was performed using Pyrobest DNA polymerase (manufactured by TAKARA BIO INC.), and reaction conditions were in accordance with the protocol recommended by the manufacturer. After digesting the PCR fragment with the restriction enzymes BglII and BclI, the PCR fragment and the above polylinker were ligated together to prepare a DNA fragment of about 400 bp. A DNA Ligation Kit Ver. 2.1 (manufactured by TAKARA BIO INC.) was used in the ligation reaction, and reaction conditions were in accordance with the protocol recommended by the manufacturer. Subsequently, a fragment of about 9.2 kbp that had been excised from the known plasmid pAYC32 (J. Gen. Microbiol., 137, 169-178 (1991)) with the restriction enzymes EcoRI and BamHI was collected, and the above DNA fragment was inserted therein to construct an expression plasmid pAYCTER3 that functions in *M. methylotrophus* ATCC 53528. The structure of the pAYCTER3 lacks the 5' side upstream sequence of the strA gene included in pAYC32, but it has instead a pUC19 multi-cloning site and an rrnB terminator and includes a beta-lactamase gene derived from *E. coli*.

(2) Secretory Expression of Beta-Lactamase in *Methylophilus methylotrophus* ATCC 53528

*Methylophilus methylotrophus* ATCC 53528 was transformed with pAYCTER3 constructed in above (1), and a strain that grew in SEIIA agar medium (5 g of ammonium sulfate, 1.9 g of $K_2HPO_4$, 1.56 g of $NaH_2PO_4 \cdot 2H_2O$, 200 mg of magnesium sulfate, 72 mg of calcium chloride, 5 µg of copper sulfate, 25 µg of manganese sulfate, 23 µg of zinc sulfate, 9.7 mg of iron trichloride, and 15 g of agar were dissolved in water up to 1 L, and the solution was adjusted to pH 7.0) containing 25 mg/l ampicillin and 1% methanol was selected. Subsequently, the selected *M. methylotrophus* ATCC 53528 having pAYCTER3 was cultured in SEIIA liquid medium containing 25 mg/l ampicillin and 2% methanol at 37° C. for 48 hours. After completion of culture, the culture supernatant of the bacterial cells of *M. methylotrophus* ATCC 53528 having pAYCTER3 was subjected to SDS-PAGE, to thereby detect a protein having the same molecular weight as beta-lactamase in the culture supernatant. Determination of the N-terminal sequence of the protein using a protein sequencer PPSQ-21 A (manufactured by Shimadzu Corporation) revealed that the sequence was a mature type of beta-lactamase, and it was confirmed that beta-lactamase was secreted in the culture supernatant.

Example 2

Secretory Expression of Phytase Derived from *Escherichia coli* K-12 Strain in *Methylophilus methylotrophus* ATCC 53528

(1) Acquisition of Methanol Dehydrogenase Gene Derived from *Methylophilus methylotrophus* ATCC 53528

The sequence of a methanol dehydrogenase gene derived from *M. methylotrophus* W3A1 strain has already been determined [Genbank Accession No. U41040]. Based on the sequence, the primers shown in SEQ ID NOS: 1 and 2 were synthesized, and a region encoding a methanol dehydrogenase sequence was amplified by the PCR method from chromosomal DNA of the *M. methylotrophus* ATCC 53528 prepared in accordance with the method of Saito and Miura. PCR was performed using Pyrobest DNA polymerase (manufactured by TAKARA BIO INC.), and the reaction condition was in accordance with the protocol recommended by the manufacturer.

Subsequently, the amplified DNA fragment of about 1.0 kb was allowed to react using Random Primer DNA Labeling Kit Ver.2 (manufactured by TAKARA BIO INC.) and [α-32P] dCTP in accordance with the protocol attached to the kit, to thereby create a DNA probe. Southern blot hybridization was performed using the prepared probe and chromosomal DNA of *M. methylotrophus* ATCC 53528 in accordance with a general method as described in Molecular Cloning 2nd edition [J. Sambrook, E. F. Fritsch and T. Maniatis, Cold Spring Harbor Laboratory Press, p 9.31 (1989)], and it was found that fragment of about 5.5 kb that had been excised with a restriction enzyme PvuII included a methanol dehydrogenase gene. Then, the fragment of about 5.5 kb obtained by digesting the chromosomal DNA of *M. methylotrophus* ATCC 53528 with PvuII was recovered after agarose gel electrophoresis using EASYTRAP Ver. 2 (manufactured by TAKARA BIO INC.), and inserted into the SmaI site in pUC18 (manufactured by TAKARA BIO INC.), and the obtained plasmid was introduced into competent cells of *Escherichia coli* JM109 (manufactured by TAKARA BIO INC.), to thereby prepare a library.

Screening of the library was performed by colony hybridization described in Molecular Cloning 2nd edition [J. Sambrook, E. F. Fritsch and T. Maniatis, Cold Spring Harbor Laboratory Press, p 1.90 (1989)] using the DNA probe of methanol dehydrogenase prepared as described above, to thereby yield a strain having a plasmid in which a methanol dehydrogenase gene fragment was cloned. Then, the plasmid was recovered from the strain and was named pUMDH. Determination of the nucleotide sequence of a fragment cloned in pUMDH revealed that the methanol dehydrogenase gene of *M. methylotrophus* ATCC 53528 had a nucleotide sequence not less than 95% homologous to a methanol dehydrogenase gene of *M. methylotrophus* W3 μl strain (SEQ ID NO: 13). Determination of the nucleotide sequence revealed that the PvuII fragment of about 5.5 kb included a full-length methanol dehydrogenase gene and a region of about 2.5 kb upstream of the 5'-side of the gene. The nucleotide sequence was determined using a dye terminator cycle sequencing kit (manufactured by PE Applied Biosystems) and a DNA sequencer 373A (manufactured by PE Applied Biosystems).

(2) Acquisition of a Phytase Gene Derived from *Escherichia coli* K-12 Strain and Construction of a Secretory Expression Plasmid The sequence of phytase gene derived from *Escherichia coli* K-12 strain has already been determined (Genbank Accession No. AE000200: SEQ ID NO: 15). Based on the sequence, the primers shown in SEQ ID NOS: 7 and 8 were synthesized, and a region encoding a phytase sequence (mature type) was amplified by the PCR method from chromosomal DNA of the *Escherichia coli* K-12 strain prepared in accordance with the method of Saito and Miura. PCR was performed using Pyrobest DNA polymerase (manufactured by TAKARA BIO INC.), and the reaction condition was in accordance with the protocol recommended by the manufacturer.

Subsequently, the promoter region and signal sequence region of methanol dehydrogenase were amplified by the PCR method using the primers shown in SEQ ID NOS: 9 and 10 from chromosomal DNA of *M. methylotrophus* ATCC 53528 prepared in accordance with the method of Saito and Miura. PCR was performed using Pyrobest DNA polymerase (manufactured by TAKARA BIO INC.), and the reaction condition was in accordance with the protocol recommended by the manufacturer. The primer shown in SEQ ID NO: 10 includes a sequence encoding the N-terminal side amino acid sequence of phytase in order to construct a fusion gene with phytase.

Thereafter, 1 μl each of the PCR solution containing a region encoding the phytase sequence (mature type) of *Escherichia coli* K-12 strain amplified as described above and the PCR solution containing the promoter region and signal sequence region of *Methylophilus methylotrophus* ATCC 53528 amplified as described above were mixed to prepare a template, and crossover PCR was performed using the primers of SEQ ID NOS: 9 and 8 to amplify a phytase fusion gene that is connected to the promoter and signal sequence of a methanol dehydrogenase gene of *Methylophilus methylotrophus* ATCC 53528. Agarose gel electrophoresis detected an amplified fragment of about 2.4 kb. The fragment was recovered from the agarose gel using EASYTRAP Ver.2 (manufactured by TAKARA BIO INC.) and inserted into the SmaI site in pHSG398 (manufactured by TAKARA BIO INC.), to thereby yield pHSGMappA. Determination of the nucleotide sequence of the inserted fragment confirmed the construction of the anticipated fusion gene. Subsequently, a BamHI-KpnI fragment of pHSGMappA was recovered from the agarose gel using EASYTRAP Ver.2 (manufactured by TAKARA BIO INC.), and the ends of the fragment were blunt-ended using a DNA blunting kit (manufactured by TAKARA BIO INC.). Thereafter, an EcoRI fragment of pAYCTER3 constructed in Example 1 (1) was recovered from the agarose gel using EASYTRAP Ver.2 (manufactured by TAKARA BIO INC.), and the ends of the fragment were blunt-ended using a DNA blunting kit (manufactured by TAKARA BIO INC.), followed by insertion of the blunt-ended BamHI-KpnI fragment, to thereby yield pAYCMappA. Determination of the nucleotide sequence of the inserted fragment confirmed the construction of the anticipated heterologous fusion gene.

(3) Expression of the phytase gene in *Methylophilus methylotrophus* ATCC 53528

*Methylophilus methylotrophus* ATCC 53528 was transformed with pAYCMappA (obtained by connecting the promoter sequence and signal sequence of methanol dehydrogenase derived from *Methylophilus methylotrophus* ATCC 53528 to the phytase gene derived from *Escherichia coli* K-12 strain) constructed in above (2) and with pAYCTER3 (control), respectively, and strains that grew in SEIIA agar medium (5 g of ammonium sulfate, 1.9 g of $K_2HPO_4$, 1.56 g of $NaH_2PO_4.2H_2O$, 200 mg of magnesium sulfate, 72 mg of calcium chloride, 5 μg of copper sulfate, 25 μg of manganese sulfate, 23 μg of zinc sulfate, 9.7 mg of iron trichloride, and 15 g of agar were dissolved in water to 1 L, and the solution was adjusted to pH 7.0) containing 25 mg/l ampicillin and 1% methanol were selected. Subsequently, the selected *M. methylotrophus* ATCC 53528 strains having pAYCMappA or pAYCTER3 were cultured in SEIIA liquid medium containing 25 mg/l ampicillin and 2% methanol at 37° C. for 48 hours. After completion of culture, the culture supernatants of bacterial cells of *M. methylotrophus* ATCC 53528 strains having pAYCMappA or pAYCTER3 were subjected to SDS-PAGE, and as a result, a protein having an objective molecular weight was detected only in the culture supernatant of the strain having pAYCMappA. Subsequently, the culture supernatants of the strains were used as crude enzyme solutions to determine phytase activity. The enzymatic activity was determined in accordance with the published report (J AOAC Int. 1994 May-June; 77(3):760-4.). As a result, in the case of *M. methylotrophus* ATCC 53528 having pAYCTER3, the enzymatic activity was not detected in the culture supernatant, while in the case of *M. methylotrophus* ATCC 53528 having pAYCMappA, the enzymatic activity was detected (60 FTU/ mL, 37° C., pH 5.5) in the culture supernatant, which revealed that the strain secreted phytase in the culture supernatant.

Example 3

Secretory Expression of an Acid Phosphatase Derived from *Morganella morganii* Strain in *Methylophilus methylotrophus* ATCC 53528

(1) Acquisition of an Acid Phosphatase Gene Derived from *Morganella morganii* Strain and Construction of a Plasmid for Secretory Expression The sequence of an acid phosphatase gene derived from *Morganella morganii* strain has already been determined (Genbank Accession No. AB035805: SEQ ID NO: 25). Based on the sequence, the primers shown in SEQ ID NOS: 27 and 28 were synthesized, and a region encoding an acid phosphatase sequence (mature type) was amplified by the PCR method from chromosomal DNA of the *Morganella morganii* strain prepared in accordance with the method of Saito and Miura. PCR was performed using Pyrobest DNA polymerase (manufactured by TAKARA BIO INC.), and the reaction condition was in accordance with the protocol recommended by the manufacturer. The primer shown in SEQ ID NO: 27 includes a sequence encoding the C-terminal side amino acid sequence in the signal sequence of methanol dehydrogenase in order to construct a fusion gene with methanol dehydrogenase of *M. methylotrophus*.

Subsequently, a region including the promoter region and signal sequence region of methanol dehydrogenase was amplified by the PCR method using the primers shown in SEQ ID NOS: 9 and 29 from chromosomal DNA of *M. methylotrophus* ATCC 53528 prepared in accordance with the method of Saito and Miura. PCR was performed using Pyrobest DNA polymerase (manufactured by TAKARA BIO INC.), and the reaction condition was in accordance with the protocol recommended by the manufacturer.

Thereafter, 1 µl each of PCR solution containing a region encoding the acid phosphatase sequence (mature) of *Morganella morganii* strain amplified as described above and the PCR solution containing the fragment of the promoter region and signal sequence region of *Methylophilus methylotrophus* ATCC 53528 amplified as described above were mixed to prepare a template, and crossover PCR was performed using the primers of SEQ ID NOS: 9 and 28 to amplify an acid phosphatase fusion gene connected to the promoter and signal sequence of a methanol dehydrogenase gene of *Methylophilus methylotrophus* ATCC 53528. Agarose gel electrophoresis detected an amplified fragment of about 1.8 kb. The fragment was recovered from the agarose gel using EASYTRAP Ver.2 (manufactured by TAKARA BIO INC.) and inserted into the SmaI site in pHSG398 (manufactured by TAKARA BIO INC.), to thereby yield pHSGMphoC. Determination of the nucleotide sequence of the inserted fragment confirmed the construction of the anticipated fusion gene. The nucleotide sequence was determined using a dye terminator cycle sequencing kit (manufactured by PE Applied Biosystems) and a DNA sequencer 373A (manufactured by PE Applied Biosystems). Subsequently, a BamHI-KpnI fragment of pHSGMphoC was recovered from the agarose gel using EASYTRAP Ver.2 (manufactured by TAKARA BIO INC.), and the ends of the fragment were blunt-ended using a DNA blunting kit (manufactured by TAKARA BIO INC.). Thereafter, a SmaI fragment of pAYCTER3 constructed in Example 1 (1) was recovered from the agarose gel using EASYTRAP Ver.2 (manufactured by TAKARA BIO INC.), and followed by insertion of the blunt-ended BamHI-KpnI fragment, to thereby yield pAYCMphoC. Determination of the nucleotide sequence of the inserted fragment confirmed the construction of the anticipated heterologous fusion gene.

(2) Expression of the Acid Phosphatase Gene in *Methylophilus methylotrophus* ATCC 53528

*Methylophilus methylotrophus* ATCC 53528 was transformed with pAYCMphoC (obtained by connecting the promoter sequence and signal sequence of methanol dehydrogenase derived from *Methylophilus methylotrophus* ATCC 53528 to the acid phosphatase gene derived from *Morganella morganii* strain) constructed in above (1) and with pAYCTER3 (control), respectively, and strains that grew in SEIIA agar medium containing 25 mg/l ampicillin and 1% methanol were selected. Subsequently, the selected *M. methylotrophus* ATCC 53528 strains having pAYCMphoC or pAYCTER3 were cultured in SEIIA liquid medium containing 25 mg/l ampicillin and 2% methanol at 37° C. for 48 hours. After completion of culture, the culture supernatants of bacterial cells of *M. methylotrophus* ATCC 53528 strains having pAYCMphoC or pAYCTER3 were subjected to SDS-PAGE, and as a result, a protein having an objective molecular weight of about 25 kDa was detected only in the culture supernatant of the strain having pAYCMphoC. Subsequently, the culture supernatants of the strains were used as crude enzyme solutions using substrate pNPP to determine phosphatase activity. As a result, in the case of *M. methylotrophus* ATCC 53528 having pAYCTER3, the enzymatic activity was not detected in the culture supernatant, while in the case of *M. methylotrophus* ATCC 53528 having pAYCMappA, the enzymatic activity was detected in the culture supernatant, which revealed that the strain secreted acid phosphatase in the culture supernatant.

Example 4

Secretory Expression of a Signal Sequence-Substituted Phytase Derived from *Escherichia coli* K-12 strain in *Methylophilus methylotrophus* ATCC 53528

(1) Construction of a Secretory Expression Plasmid for Signal Sequence-Substituted Phytase Derived from *Escherichia coli* K-12 Strain The promoter region of methanol dehydrogenase was amplified by the PCR method using the primers shown in SEQ ID NOS: 30 and 31 from chromosomal DNA of *M. methylotrophus* ATCC 53528 prepared in accordance with the method of Saito and Miura. PCR was performed using Pyrobest DNA polymerase (manufactured by TAKARA BIO INC.), and the reaction condition was in accordance with the protocol recommended by the manufacturer. The primer shown in SEQ ID NO: 30 includes a recognition sequence of a restriction enzyme Hind III.

In order to use a signal sequence of the phytase derived from *E. coli* K-12 strain, a phytase gene including a signal sequence was amplified by the PCR method using the primers shown in SEQ ID NOS: 32 and 33 from chromosomal DNA of *E. coli* K-12 strain prepared in accordance with the method of Saito and Miura. PCR was performed using Pyrobest DNA polymerase (manufactured by TAKARA BIO INC.), and the reaction condition was in accordance with the protocol recommended by the manufacturer. The primer shown in SEQ ID NO: 32 includes a sequence encoding C-terminal side amino acid sequence in the promoter sequence of methanol dehydrogenase in order to construct a fusion gene with the methanol dehydrogenase of *M. methylotrophus*, and the primer shown in SEQ ID NO: 33 includes a recognition sequence of a restriction enzyme KpnI.

Thereafter, 1 μl each of PCR solution containing a region encoding the phytase sequence of *Escherichia coli* K-12 strain amplified as described above and the PCR solution containing the promoter region of *Methylophilus methylotrophus* ATCC 53528 amplified as described above were mixed to prepare a template, and crossover PCR was performed using the primers of SEQ ID NOS: 30 and 33 to amplify a fusion gene of a signal sequence and a mature gene of *E. coli* phytase which was connected to the promoter of a methanol dehydrogenase gene of *Methylophilus methylotrophus* ATCC 53528. Agarose gel electrophoresis detected an amplified fragment of about 2.4 kb. The HindIII-KpnI fragment was recovered from the agarose gel using EASYTRAP Ver.2 (manufactured by TAKARA BIO INC.) and inserted into the HindIII-KpnI site in pAYCTER3 of Example 1 (1), to thereby yield pAYCAappA. Determination of the nucleotide sequence of the inserted fragment confirmed the construction of the anticipated fusion gene. The nucleotide sequence was determined using a dye terminator cycle sequencing kit (manufactured by PE Applied Biosystems) and a DNA sequencer 373A (manufactured by PE Applied Biosystems).

On the other hand, in order to use a signal sequence of acid phosphatase of *Morganella morganii* strain, an acid phosphatase gene including a signal sequence was amplified by the PCR method using the primers shown in SEQ ID NOS: 34 and 28 from chromosomal DNA of *M. morganii* strain prepared in accordance with the method of Saito and Miura. PCR was performed using Pyrobest DNA polymerase (manufactured by TAKARA BIO INC.), and the reaction condition was in accordance with the protocol recommended by the manufacturer. The primer shown in SEQ ID NO: 34 includes a sequence encoding C-terminal side amino acid sequence in the promoter sequence of methanol dehydrogenase in order to construct a fusion gene with methanol dehydrogenase of *M. methylotrophus*.

1 μl each of the PCR solution containing the acid phosphatase gene amplified as described above and the PCR solution containing the above-mentioned promoter region of methanol dehydrogenase were mixed to prepare a template, and crossover PCR was performed using the primers of SEQ ID NOS: 30 and 28 to amplify a fusion gene of a signal sequence and a mature type of acid phosphatase of *M. morganii* which was connected to the promoter of a methanol dehydrogenase gene of *M. methylotrophus* ATCC 53528. Moreover, a fragment comprising the promoter of the methanol dehydrogenase gene of *M. methylotrophus* ATCC 53528 and the signal sequence of acid phosphatase of *M. morganii* was amplified using the fusion gene as a template and using the primers shown in SEQ ID NOS: 30 and 35. The primer shown in SEQ ID NO: 35 includes a sequence encoding the N-terminal side amino acid sequence in a phytase mature sequence in order to construct a fusion gene with *E. coli* phytase.

1 μl each of the PCR solution containing the fusion gene of the promoter region of methanol dehydrogenase and the signal sequence of acid phosphatase amplified as described above and the PCR solution containing the phytase gene amplified in Example 2 (2) were mixed to prepare a template, and crossover PCR was performed using the primers of SEQ ID NOS: 30 and 33 to amplify a fusion gene of the signal sequence of acid phosphatase of *M. morganii* and a mature type of *E. coli* phytase which was connected to the promoter of the methanol dehydrogenase gene of *M. methylotrophus* ATCC 53528. Agarose gel electrophoresis detected an amplified fragment of about 2.4 kb. The amplified fragment was treated with restriction enzymes HindIII and KpnI, and the HindIII-KpnI fragment was recovered from the agarose gel using EASYTRAP Ver.2 (manufactured by TAKARA BIO INC.) and inserted into the HindIII-KpnI site in pAYCTER3 obtained in Example 1 (1), to thereby yield pAYCCappA. Determination of the nucleotide sequence of the inserted fragment confirmed the construction of the anticipated fusion gene. The nucleotide sequence was determined using a dye terminator cycle sequencing kit (manufactured by PE Applied Biosystems) and a DNA sequencer 373A (manufactured by PE Applied Biosystems).

(2) Expression of an *E. coli* Mature Type Phytase Connected to the Signal Sequence of Phytase of *E. coli* or the Signal Sequence of Acid Phosphatase of *M. morganii* in *Methylophilus methylotrophus* ATCC 53528

*M. methylotrophus* ATCC 53528 was transformed respectively with pAYCAappA constructed in above (1) (obtained by connecting the promoter sequence of methanol dehydrogenase derived from *M. methylotrophus* ATCC 53528 and the signal sequence of phytase derived from *E. coli* to a mature type gene), with pAYCCappA (obtained by connecting the promoter sequence of methanol dehydrogenase derived from *M. methylotrophus* ATCC 53528 and the signal sequence of acid phosphatase derived from *M. morganii* to the mature type gene of phytase derived from *E. coli*), and with pAYCTER3 (control), and strains that grew in SEIIA agar medium containing 25 mg/l ampicillin and 1% methanol were selected. Subsequently, the selected *M. methylotrophus* ATCC 53528 strains having pAYCAappA, pAYCCappA, or pAYCTER3 were cultured in SEIIA liquid medium containing 25 mg/l ampicillin and 2% methanol at 37° C. for 48 hours. After completion of culture, the culture supernatants of bacterial cells of *M. methylotrophus* ATCC 53528 strains having pAYCAappA, pAYCCappA, or pAYCTER3 were subjected to SDS-PAGE, and as a result, a protein having an objective molecular weight was detected only in the culture supernatants of the strain having pAYCAappA and the strain having pAYCCappA. Subsequently, the culture supernatants of the strains were used as crude enzyme solutions to determine phytase activity. As a result, in the case of *M. methylotrophus* ATCC 53528 having pAYCTER3, the enzymatic activity was not detected in the culture supernatant, while in the cases of *M. methylotrophus* ATCC 53528 having pAYCAappA or pAYCCappA, the enzymatic activities were detected in the culture supernatants, which revealed that the strains secreted phytase in the culture supernatants. The enzymatic activity was determined by the same method as described in Example 2 above.

Example 5

Secretory Expression of a Promoter-Substituted Phytase Derived from *Escherichia coli* K-12 Strain in *Methylophilus methylotrophus* ATCC 53528

(1) Construction of a Secretory Expression Plasmid for Promoter-Substituted Phytase Derived from *Escherichia coli* K-12 Strain In order to use a tac promoter, a tac promoter region was amplified by the PCR method using pKK223-3 (manufactured by Pharmacia) as a template and using the primers shown in SEQ ID NOS: 36 and 37. The sequence of the tac promoter is shown in SEQ ID NO: 12. PCR was performed using Pyrobest DNA polymerase (manufactured by TAKARA BIO INC.), and the reaction condition was in accordance with the protocol recommended by the manufacturer. The primer shown in SEQ ID NO: 36 includes a recognition sequence of a restriction enzyme EcoRI.

A fusion gene of a signal sequence of methanol dehydrogenase derived from *M. methylotrophus* and phytase derived from *E. coli* (mature) was amplified by the PCR method using pAYCMappA obtained in Example 2 (2) as a template and using the primers shown in SEQ ID NOS: 38 and 39. PCR was performed using Pyrobest DNA polymerase (manufactured by TAKARA BIO INC.), and the reaction condition was in accordance with the protocol recommended by the manufacturer. The primer shown in SEQ ID NO: 38 includes a partial sequence of the tac promoter in order to construct a fusion gene with the tac promoter, while the primer shown in SEQ ID NO: 39 includes a recognition sequence of a restriction enzyme EcoRI.

Subsequently, 1 µl each of PCR solution containing a region encoding the tac promoter sequence amplified as described above and the PCR solution containing a region encoding a fusion gene of a signal sequence of methanol dehydrogenase derived from *M. methylotrophus* and phytase derived from *E. coli* (mature) amplified as described above were mixed to prepare a template, and crossover PCR was performed using the primers of SEQ ID NOS: 36 and 39 to amplify a fusion gene of the signal sequence of methanol dehydrogenase derived from *M. methylotrophus* connected to the tac promoter and the mature type of phytase derived from *E. coli*. Agarose gel electrophoresis detected an amplified fragment of about 1.6 kb. The amplified fragment was treated with EccRI, and the EcoRI fragment was recovered from the agarose gel using EASYTRAP Ver.2 (manufactured by TAKARA BIO INC.) and inserted into EcoRI site in pAYCTER3 obtained in Example 1 (1), to thereby yield pAYCPtacMappA. Determination of the nucleotide sequence of the inserted fragment confirmed the construction of the anticipated fusion gene. The nucleotide sequence was determined using a dye terminator cycle sequencing kit (manufactured by PE Applied Biosystems) and a DNA sequencer 373A (manufactured by PE Applied Biosystems).

(2) Expression of a Phytase Derived from *E. coli* Connected to tac Promoter in *Methylophilus methylotrophus* ATCC 53528

*M. methylotrophus* ATCC 53528 was transformed with pAYCPtacMappA constructed in above (1) (obtained by connecting the tac promoter sequence and the signal sequence of methanol dehydrogenase derived from *Methylophilus methylotrophus* ATCC 53528 to the mature type gene of phytase derived from *E. coli*) and with pAYCTER3 (control), and strains that grew in SEIIA agar medium containing 25 mg/l ampicillin and 1% methanol were selected. Subsequently, the selected *M. methylotrophus* ATCC 53528 strains having pAYCPtacMappA or pAYCTER3 were cultured in SEIIA liquid medium containing 25 mg/l ampicillin and 2% methanol at 37° C. for 48 hours. After completion of culture, the culture supernatants of bacterial cells of *M. methylotrophus* ATCC 53528 strains having pAYCPtacMappA or pAYCTER3 were subjected to SDS-PAGE, and as a result, a protein having an objective molecular weight was detected only in the culture supernatant of the strain having pAYCPtacMappA. Subsequently, the culture supernatants of the strains were used as crude enzyme solutions to determine phytase activity. As a result, in the case of *M. methylotrophus* ATCC 53528 having pAYCTER3, the enzymatic activity was not detected in the culture supernatant, while in the case of *M. methylotrophus* ATCC 53528 having pAYCPtacMappA, the enzymatic activity was detected in the culture supernatant, which revealed that the strain secreted phytase in the culture supernatant. The enzymatic activity was determined by the same method as that described in Example 2 above.

Example 6

Secretory Expression of a Beta-Lactamase Derived from *Escherichia coli* K-12 Strain in *Methylobacillus glycogenes* ATCC 29475

(1) Construction of an Expression Plasmid pAYCTER-tet that Functions in *Methylobacillus glycogenes* ATCC 29475

*M. glycogenes* ATCC 29475 strain has resistance to ampicillin and streptomycin and has sensitivity to tetracycline, so a tetracycline-resistance gene was introduced into the secretory expression plasmid pAYCTER3 produced in Example 1 (1). That is, a tetracycline-resistant gene was amplified by the PCR method using pRK310 (described in Plasmid. 1985 March; 13(2): 149-53) as a template and using primers of SEQ ID NOS: 23 and 24. Agarose gel electrophoresis detected an amplified fragment of about 1.5 kb. The amplified fragment was treated with a restriction enzyme BamHI and recovered from the agarose gel using EASYTRAP Ver.2 (manufactured by TAKARA BIO INC.), and inserted into the BamHI site in pAYCTER3 obtained in Example 1 (1), to thereby yield pAYCTER-tet. Determination of the nucleotide sequence of the inserted fragment confirmed the construction of the anticipated fusion gene. The primers shown in SEQ ID NOS: 23 and 24 include recognition sequences of the restriction enzyme BamHI, and the nucleotide sequence was determined using a dye terminator cycle sequencing kit (manufactured by PE Applied Biosystems) and a DNA sequencer 373A (manufactured by PE Applied Biosystems).

(2) Secretory Expression of the Beta-Lactamase in *Methylobacillus glycogens* ATCC 29475

*Methylobacillus glycogens* ATCC 29475 was transformed within pAYCTER-tet constructed in (1) above, and a strain that grew with SEIIA agar medium (5 g of ammonium sulfate, 1.9 g of K$_2$HPO$_4$, 1.56 g of NaH$_2$PO$_4$.2H$_2$O, 200 mg of magnesium sulfate, 72 mg of calcium chloride, 5 µg of copper sulfate, 25 µg of manganese sulfate, 23 µg of zinc sulfate, 9.7 mg of iron trichloride, and 15 g of agar were dissolved in water to 1 L, and the solution was adjusted to pH 7.0) containing 5 mg/l tetracycline and 1% methanol was selected. Subsequently, the selected *M. glycogens* ATCC 29475 having pAYCTER-tet was cultured in SEIIA liquid medium containing 5 mg/l tetracycline and 2% methanol at 30° C. for 48 hours. After completion of culture, the culture supernatant of the bacterial cells of *M. glycogens* ATCC 29475 having pAYCTER-tet was subjected to SDS-PAGE, to thereby detect a protein having the same molecular weight as beta-lactamase in the culture supernatant. Determination of the N-terminal sequence of the protein using a protein sequencer PPSQ-21 A (manufactured by Shimadzu Corporation) revealed that the sequence was a mature sequence of beta-lactamase, and it was confirmed that beta-lactamase was secreted in the culture supernatant.

Example 7

Secretory Expression of a Phytase Derived from *Escherichia coli* K-12 Strain in *Methylobacillus glycogenes* ATCC 29475

(1) Construction of a Secretory Expression Plasmid for Phytase Derived from *Escherichia coli* K-12 strain in *Methylobacillus glycogenes* ATCC 29475

In order to perform secretory expression of phytase derived from *E. coli* in *M. glycogenes* ATCC 29475 strain, a BamHI-treated fragment of the tetracycline-resistant gene produced in Example 6 (1) was inserted into the BamHI site in the phytase secretory expression plasmid pAYCPtacMappA produced in Example 5 (1), to thereby yield pAYCPtacMappA-tet. Determination of the nucleotide sequence of the inserted fragment confirmed the construction of the anticipated fusion gene. The nucleotide sequence was determined using a dye terminator cycle sequencing kit (manufactured by PE Applied Biosystems) and a DNA sequencer 373A (manufactured by PE Applied Biosystems). Expression of a phytase derived from *E. coli* in *Methylobacillus glycogenes* ATCC 29475

*Methylobacillus glycogenes* ATCC 29475 was transformed with pAYCPtacMappA-tet constructed in (1) above or with pAYCTER-tet prepared in Example 6 (2) (control), and strains that grew in SEIIA agar medium containing 5 mg/l tetracycline and 1% methanol were selected. Subsequently, the selected *M. glycogenes* ATCC 29475 strains having pAYCPtacMappA-tet or pAYCTER-tet were cultured in SEIIA liquid medium containing 5 mg/l tetracycline and 2% methanol at 37° C. for 48 hours. After completion of culture, the culture supernatants of bacterial cells of *M. glycogenes* ATCC 29475 strains having pAYCPtacMappA-tet or pAYCTER-tet were subjected to SDS-PAGE, and as a result, a protein having an objective molecular weight was detected only in the culture supernatant of the strain having pAYCPtacMappA-tet. Subsequently, the culture supernatants of the strains were used as crude enzyme solutions to determine phytase activity. As a result, in the case of *M. glycogenes* ATCC 29475 having pAYCTER-tet, the enzymatic activity was not detected in the culture supernatant, while in the case of *M. glycogenes* ATCC 29475 having pAYCPtacMappA-tet, the enzymatic activity was detected in the culture supernatant, which revealed that the strain secreted phytase in the culture supernatant. The enzymatic activity was determined by the same method as that described in Example 2 above.

INDUSTRIAL APPLICABILITY

According to the present invention, secretory production of a protein can be performed efficiently and at low cost. In particular, secretory production of an industrially useful protein, e.g., phytase or the like can be performed.

The invention claimed is:

1. A method of producing a protein, comprising culturing an obligate methanol-assimilating bacterium in a liquid medium containing methanol as a major carbon source to allow the bacterium to secrete the target protein out of the bacterial cells, and recovering the secreted target protein from the liquid medium, wherein said bacterium harbors a DNA construct which contains a promoter sequence that functions in the methanol-assimilating bacterium and a nucleotide sequence that encodes a polypeptide containing a signal sequence and a target protein sequence which is operably connected to the promoter sequence, wherein said obligate methanol-assimilating bacterium is selected from the group consisting of *Methylophilus methylotrophus* and *Methylobacillus glycogenes*, and wherein the signal sequence has the amino acid sequence of SEQ ID NO: 18.

2. The method according to claim 1, wherein the promoter sequence that functions in the methanol-assimilating bacterium is selected from the group consisting of a methanol dehydrogenase promoter, a tac promoter, a σE promoter, and a ribosomal protein promoter.

3. The method according to claim 1, wherein the promoter sequence is a nucleotide sequence selected from the group consisting of SEQ ID NO: 11, SEQ ID NO: 12, SEQ ID NO: 21, and SEQ ID NO: 22.

4. The method according to claim 1, wherein the protein is selected from the group consisting of phytase, interleukin, transglutaminase, interferon, insulin, acid phosphatase, and peptide synthase.

5. The method according to claim 1, wherein the obligate methanol-assimilating bacterium is *Methylophilus methylotrophus*.

6. The method according to claim 1, wherein the obligate methanol-assimilating bacterium is *Methylobacillus glycogenes*.

7. A method of producing a protein, comprising culturing an obligate methanol-assimilating bacterium in a liquid medium containing methanol as a major carbon source to allow the bacterium to secrete the target protein out of the bacterial cells, and recovering the secreted target protein from the liquid medium, wherein said bacterium harbors a DNA construct which contains a promoter sequence that functions in the methanol-assimilating bacterium and a nucleotide sequence that encodes a polypeptide containing a signal sequence and a target protein sequence which is operably connected to the promoter sequence, wherein said obligate methanol-assimilating bacterium is selected from the group consisting of *Methylophilus methylotrophus* and *Methylobacillus glycogenes*, and wherein the promoter sequence is a nucleotide sequence selected from the group consisting of SEQ ID NO: 11, SEQ ID NO: 12, SEQ ID NO: 21, and SEQ ID NO: 22.

8. The method according to claim 7, wherein the signal sequence is a signal sequence of a protein selected from the group consisting of methanol dehydrogenase, phytase, and acid phosphatase.

9. The method according to claim 7, wherein the protein is selected from the group consisting of phytase, interleukin, transglutaminase, interferon, insulin, acid phosphatase, and peptide synthase.

10. The method according to claim 7, wherein the obligate methanol-assimilating bacterium is *Methylophilus methylotrophus*.

11. The method according to claim 7, wherein the obligate methanol-assimilating bacterium is *Methylobacillus glycogenes*.

* * * * *